(12) United States Patent
Shoji et al.

(10) Patent No.: US 8,987,440 B2
(45) Date of Patent: *Mar. 24, 2015

(54) CYCLIC CARBODIIMIDE COMPOUNDS

(75) Inventors: Shinichiro Shoji, Iwakuni (JP); Hirotaka Suzuki, Iwakuni (JP)

(73) Assignee: Teijin Limited, Osaka (JP)

( * ) Notice: Subject to any disclaimer, the term of this patent is extended or adjusted under 35 U.S.C. 154(b) by 301 days.

This patent is subject to a terminal disclaimer.

(21) Appl. No.: 13/139,103

(22) PCT Filed: Dec. 15, 2009

(86) PCT No.: PCT/JP2009/071190
§ 371 (c)(1),
(2), (4) Date: Jun. 10, 2011

(87) PCT Pub. No.: WO2010/071211
PCT Pub. Date: Jun. 24, 2010

(65) Prior Publication Data
US 2011/0251384 A1    Oct. 13, 2011

(30) Foreign Application Priority Data
Dec. 15, 2008  (JP) .................. 2008-318533

(51) Int. Cl.
C07D 498/02 (2006.01)
C07D 498/10 (2006.01)
C07D 273/08 (2006.01)

(52) U.S. Cl.
CPC ............ C07D 273/08 (2013.01); C07D 498/10 (2013.01)
USPC ........................................... 540/469

(58) Field of Classification Search
None
See application file for complete search history.

(56) References Cited

U.S. PATENT DOCUMENTS

| | | | |
|---|---|---|---|
| 4,576,857 A | 3/1986 | Gannett et al. | |
| 4,597,910 A | 7/1986 | Konig et al. | |
| 4,870,164 A | 9/1989 | Kuhne et al. | |
| 4,888,125 A | 12/1989 | Konig et al. | |
| 4,914,238 A | 4/1990 | Sanders | |
| 2008/0161554 A1 | 7/2008 | Dai et al. | |

FOREIGN PATENT DOCUMENTS

| CN | 1539821 A | 10/2004 |
|---|---|---|
| CN | 1175016 A | 11/2004 |
| EP | 0 270 906 A1 | 6/1988 |
| EP | 0 573 041 A1 | 12/1993 |
| EP | 1125956 A1 | 8/2001 |
| GB | 1 252 707 | 11/1971 |
| JP | 59170122 A | 9/1984 |
| JP | 6357564 A | 3/1988 |
| JP | 63159360 A | 7/1988 |
| JP | 237949 B2 | 8/1990 |
| JP | 625101 A | 4/1994 |
| JP | 6279370 A | 10/1994 |
| JP | 9-188660 A | 7/1997 |
| JP | 10-72428 A | 3/1998 |
| JP | 11-092636 | 6/1999 |
| JP | 2000143756 A | 5/2000 |
| JP | 200260644 A | 2/2002 |
| JP | 2004-332166 | 11/2004 |
| JP | 2005-002174 | 6/2005 |
| JP | 2005-350829 | 12/2005 |
| JP | 2006-220676 A | 8/2006 |
| JP | 2008-83359 A | 4/2008 |
| WO | 2005/016874 A2 | 2/2005 |
| WO | 2008081230 A1 | 7/2008 |

OTHER PUBLICATIONS

Pedro Molina et al., A New and Efficient Preparation of Cyclic Carbodiimides from Bis(iminophosphoranes) and the System Boc20/DMAP, Journal of Organic Chemistry, May 17, 1994, p. 7306-7315, vol. 59, American Chemical Society.
International Preliminary Report on Patentability issued on Jul. 5, 2011 for corresponding Application No. PCT/JP2009/071190.
Glinka et al.; A New Method of Synthesizing 8—10-Membered Heterocycle Systems Condensed With Two Aromatic Rings; Polish Journal of Chemistry, Polskie Towarzystwo Chemiczne, PL, vol. 58, Jan. 1, 1984, pp. 259-262.
Partial translation of CN1539821, Oct. 27, 2004, Univ Fudan.
Japanese Office Action in corresponding application No. 2011-136856 dated Jul. 24, 2013.
Laliberte et al.; Molecular Tectonics. Porous Hydrogen-Bonded Networks Built from Derivatives of Pentaerythrityl Tetraphenyl Ether; J. Org. Chem., 2004, vol. 69, pp. 1776-1787.

(Continued)

Primary Examiner — Noble Jarrell
(74) Attorney, Agent, or Firm — Sughrue Mion, PLLC

(57) ABSTRACT

A cyclic carbodiimide compound which is useful as an end-sealing agent for polymer compounds. The cyclic carbodiimide compound is represented by the following formula (i):

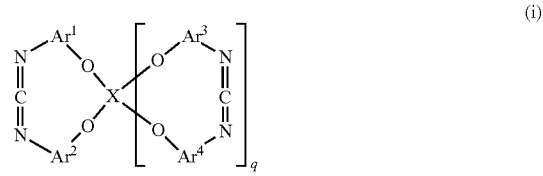

In the above formula, X is a divalent group or a tetravalent group represented by the following formula (i-4). When X is divalent, q is 0 and when X is tetravalent, q is 1. $Ar^1$ to $Ar^4$ are each independently an aromatic group. They may be substituted by an alkyl group having 1 to 6 carbon atoms or phenyl group.

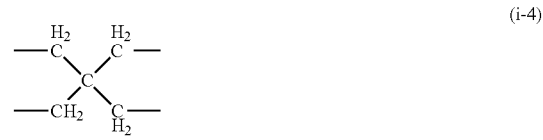

12 Claims, No Drawings

(56) References Cited

OTHER PUBLICATIONS

Ibrahim et al.; Efficient synthesis of 16-28 membered macrocyclic crown amides via ring closing metathesis; Science Direct, Tetrahedron, 59, 2003, pp. 7273-7282.

Luboch et al.; Reductive Cyclization Products of 1,2-bis(2-nitrophenoxy)ethanes. X-ray Structures of 10-membered Azoxycrown Ether Stereoisomers and the Sodium Iodide Complex of a 20-membered Azoazoxycrown; Journal of Supramolecular Chemistry, 2001, 1, pp. 101-110.

Elwahy et al.; Synthesis of the first tris(crown formazan); Science Direct, Tetrahedron Letters, 47, 2006, pp. 1303-1306.

Japanese Office Action in corresponding Application No. 2011-136855 dated Aug. 7, 2013.

Asha et al.; Relaxation Behavior of Twin Nonlinear Optical Chromophores: Effect of the Spacer Length; Chem Mater. 1999, 11, pp. 3352-3358.

Paul W. Wojtkowski; Aromatic-Aliphatic Azomethin Ether Polymers and Fibers; Macromolecules, 1987, 20, pp. 740-748.

Laliberte et al.; Molecular Tectonics. Porous Hydrogen-Bonded Networks Built from Derivatives of Pentaerythrityl Tetraphenyl Ether; J. Org. Chem. 2004, 69, pp. 1776-1787.

CYCLIC CARBODIIMIDE COMPOUNDS

CROSS REFERENCE TO RELATED APPLICATION

This application is a National Stage of International Application No. PCT/JP2009/071190 filed Dec. 15, 2009, the contents of which are incorporated herein by reference in their entirety.

TECHNICAL FIELD

The present invention relates to a cyclic carbodiimide compound.

BACKGROUND ART

Polyesters, polyamides, polyimides, polycarbonates and polyurethanes are used for various purposes because they have excellent mechanical properties. Since these polymers have a hydrolyzable ester bond, amide bond, imido bond, carbonate bond and urethane bond in the molecule, respectively, there may occur a problem with reliability when they are used in a more severe environment, and urgent countermeasures against this are awaited.

Since the catalytic hydrolysis of a hydrolyzable bond such as an ester bond is promoted when a polar group such as a carboxyl group is existent in the molecule, there is proposed a method of suppressing this disadvantage by using a sealing agent for the carboxyl group to reduce the carboxyl group concentration (Patent Document 1 and Patent Document 2).

As the sealing agent for an acid group such as a carboxyl group is used a mono- or poly-carbodiimide compound in consideration of the stability and reactivity of the sealing agent and the color of the obtained product, and some effect is obtained. However, as the mono- or poly-carbodiimide compound is a linear carbodiimide compound, a volatile isocyanate compound is by-produced at the time of its use, causing such an essential defect as the production of a bad smell, thereby deteriorating the work environment. The development of a sealing agent having higher reactivity and free from this defect is awaited.

Patent Document 3 discloses a macrocyclic carbodiimide compound having an urethane bond and a polymer chain with a molecular weight of 100 to 7,000. Since the macrocyclic carbodiimide compound has a high molecular weight, it has low efficiency as a sealing agent for acid groups. Patent Document 3 does not take into consideration the prevention of the production of a bad smell.
(Patent Document 1) JP-A 2004-332166
(Patent Document 2) JP-A 2005-350829
(Patent Document 3) WO2008/081230

DISCLOSURE OF THE INVENTION

It is an object of the present invention to provide a cyclic carbodiimide compound which is useful as a stabilizer for polymers having a hydrolyzable functional group, such as polyesters. It is another object of the present invention to provide a process of producing the cyclic carbodiimide compound. It is still another object of the present invention to provide an end-sealing agent for polymer compounds, which comprises the cyclic carbodiimide compound as an active ingredient. It is a further object of the present invention to provide a capture agent for acid groups, which comprises the cyclic carbodiimide compound as an active ingredient.

The inventors of the present invention have conducted intensive studies on a sealing agent which prevents the liberation of an isocyanate compound even when it reacts with an acid group such as carboxyl group. As a result, they have found that even when a carbodiimide compound having a cyclic structure reacts with an acid group, it does not liberate an isocyanate compound and does not produce a bad smell, thereby not deteriorating the work environment. The present invention has been accomplished based on this finding.

That is, the present invention includes the following inventions.
1. A cyclic carbodiimide compound represented by the following formula (i):

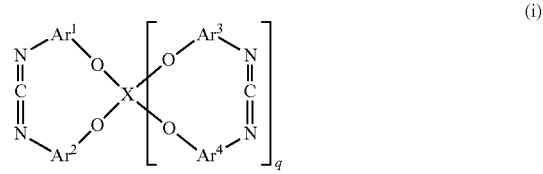

(in the above formula, X is any one of divalent groups represented by the following formulas (i-1) to (i-3) or a tetravalent group represented by the following formula (i-4), when X is divalent, q is 0 and when X is tetravalent, q is 1, and $Ar^1$ to $Ar^4$ are each independently an aromatic group and may be substituted by an alkyl group having 1 to 6 carbon atoms or phenyl group)

(in the above formula, n is an integer of 1 to 6)

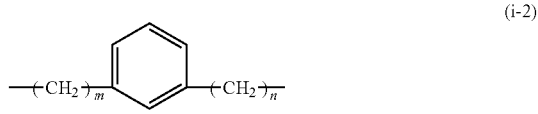

(in the above formula, m and n are each independently an integer of 0 to 3)

(in the above formula, $R^1$ and $R^2$ are each independently an alkyl group having 1 to 6 carbon atoms or phenyl group)

2. The compound in the above paragraph 1, wherein $Ar^1$ to $Ar^4$ are each independently an orthophenylene group or 1,2- naphthalene-diyl group which may be substituted by an alkyl group having 1 to 6 carbon atoms or phenyl group.

3. A process of producing the cyclic carbodiimide compound of the above paragraph 1, comprising the steps of:

(1) (1a) reacting a compound of the following formula (a-1), a compound of the following formula (a-2) and a compound of the following formula (b-1) to obtain a nitro compound represented by the following formula (c):

$$HO-Ar^1-NO_2 \quad (a\text{-}1)$$

$$HO-Ar^2-NO_2 \quad (a\text{-}2)$$

$$E^1\text{-}X\text{-}E^2 \quad (b\text{-}1)$$

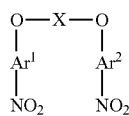

(c)

(in the above formulas, X, $Ar^1$ and $Ar^2$ are as defined in the above formula (i), and $E^1$ and $E^2$ are each independently a group selected from the group consisting of halogen atom, toluenesulfonyloxy group, methanesulfonyloxy group, benzenesulfonyloxy group and p-bromobenzenesulfonyloxy group) (examples of the halogen atom in the present invention include chlorine atom, bromine atom and iodine atom);

(2) (2a) reducing the obtained nitro compound to obtain an amine compound represented by the following formula (d):

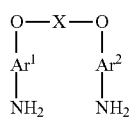

(d)

(in the above formula, $Ar^1$, $Ar^2$ and X are as defined in the above formula (i));

(3) (3a) reacting the obtained amine compound with triphenylphosphine dibromide to obtain a triphenylphosphine compound represented by the following formula (e-1):

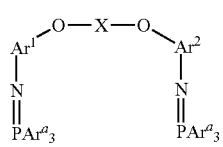

(e-1)

(in the above formula, $Ar^1$, $Ar^2$ and X are as defined in the above formula (i), and $Ar^a$ is a phenyl group); and (4) (4a) isocyanating the obtained triphenylphosphine compound in a reaction system and then decarbonating the isocyanated product directly to obtain a compound of the following formula (f):

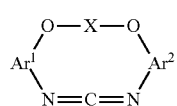

(f)

(in the above formula, $Ar^1$, $Ar^2$ and X are as defined in the above formula (i)).

4. The process in the above paragraph 3, wherein the step (1a) is the step (1b) of reacting a compound of the following formula (a-i), a compound of the following formula (a-ii) and a compound of the following formula (b-i):

$$E^3\text{-}Ar^1-NO_2 \quad (a\text{-}i)$$

$$E^4\text{-}Ar^2-NO_2 \quad (a\text{-}ii)$$

$$HO-X-OH \quad (b\text{-}i)$$

(in the above formulas, $Ar^1$, $Ar^2$ and X are as defined in the above formula (i), and $E^3$ and $E^4$ are each independently a group selected from the group consisting of halogen atom, toluenesulfonyloxy group, methanesulfonyloxy group, benzenesulfonyloxy group and p-bromobenzenesulfonyloxy group).

5. The process in the above paragraph 3 or 4, wherein the step (3a) is the step (3b) of reacting an amine compound with carbon dioxide or carbon disulfide to obtain an urea compound or thiourea compound represented by the following formula (e-2):

(e-2)

(in the above formula, $Ar^1$, $Ar^2$ and X are as defined in the above formula (i), and Z is an oxygen atom or sulfur atom); and the step (4a) is the step (4b) of dehydrating the obtained urea compound or desulfurizing the thiourea compound.

6. A process of producing the cyclic carbodiimide compound of the above paragraph 1, comprising the steps of:

(1) (1A) reacting compounds of the following formulas (A-1) to (A-4) and a compound of the following formula (B-1) to obtain a nitro compound of the following formula (C);

$$HO-Ar^1-NO_2 \quad (A\text{-}1)$$

$$HO-Ar^2-NO_2 \quad (A\text{-}2)$$

$$HO-Ar^3-NO_2 \quad (A\text{-}3)$$

$$HO-Ar^4-NO_2 \quad (A\text{-}4)$$

(B-1)

($X_1$ is

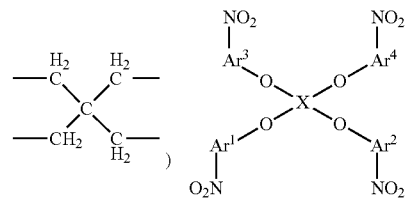

(C)

(in the above formulas, $Ar^1$ to $Ar^4$ and X are as defined in the above formula (i), and $E^1$ to $E^4$ are each independently a group selected from the group consisting of halogen atom, toluenesulfonyloxy group, methanesulfonyloxy group, benzenesulfonyloxy group and p-bromobenzenesulfonyloxy group);

(2) (2A) reducing the obtained nitro compound to obtain an amine compound of the following formula (D):

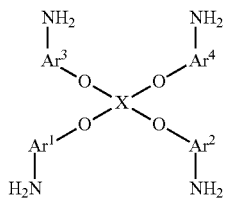

(D)

(in the above formula, $Ar^1$ to $Ar^4$ and X are as defined in the above formula (i));

(3) (3A) reacting the obtained amine compound with triphenylphosphine dibromide to obtain a triphenylphosphine compound of the following formula (E-1):

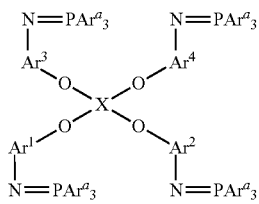

(E-1)

(in the above formula, $Ar^1$ to $Ar^4$ and X are as defined in the above formula (i), and $Ar^a$ is a phenyl group); and (4) (4A) isocyanating the obtained triphenylphosphine compound in a reaction system and then decarbonating the isocyanated product directly to obtain a compound of the following formula (F):

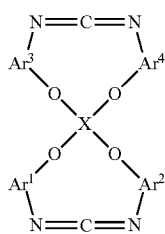

(F)

(in the above formula, $Ar^1$ to $Ar^4$ and X are as defined in the above formula (i)).

7. The process in the above paragraph 6, wherein the step (1A) is the step (1B) of reacting compounds of the following formulas (A-i) to (A-iv) and a compound of the following formula (B-i) to obtain a nitro compound of the formula (C):

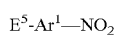  (A-i)

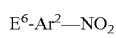  (A-ii)

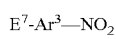  (A-iii)

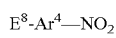  (A-iv)

(B-i)

($X_1$ is

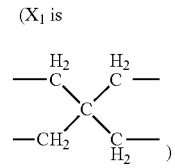

)

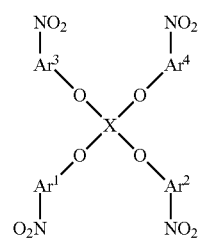

(C)

(in the above formulas, $Ar^1$ to $Ar^4$ and X are as defined in the above formula (i), and $E^5$ to $E^8$ are each independently a group selected from the group consisting of halogen atom, toluenesulfonyloxy group, methanesulfonyloxy group, benzenesulfonyloxy group and p-bromobenzenesulfonyloxy group).

8. The process in the above paragraph 6 or 7, wherein the step (3A) is the step (3B) of reacting an amine compound with carbon dioxide or carbon disulfide to obtain an urea compound or thiourea compound of the following formula (E-2):

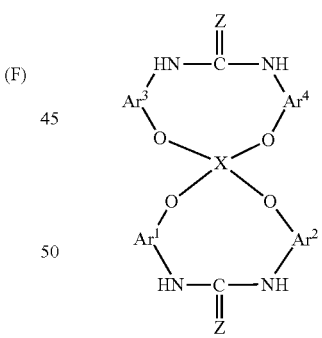

(E-2)

(in the above formula, $Ar^1$ to $Ar^4$ and X are as defined in the above formula (i), and Z is an oxygen atom or sulfur atom); and the step (4A) is the step (4B) of dehydrating the obtained urea compound or desulfurizing the thiourea compound.

9. An end-sealing agent for polymer compounds, which comprises the cyclic carbodiimide compound of the above formula (i) as an active ingredient.

10. A capture agent for an acid group, which comprises the cyclic carbodiimide compound of the above formula (i) as an active ingredient.

BEST MODE FOR CARRYING OUT THE INVENTION

<Cyclic Carbodiimide Compound>

The present invention is a cyclic carbodiimide compound represented by the following formula (i).

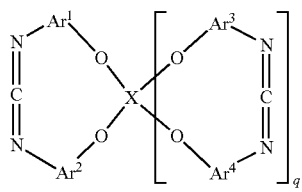

(i)

In the above formula, $Ar^1$ to $Ar^4$ are each independently an aromatic group. The aromatic group may be substituted by an alkyl group having 1 to 6 carbon atoms or phenyl group. Examples of the aromatic group include aromatic groups having 5 to 15 carbon atoms such as phenylene group and naphthalenediyl group.

Examples of the alkyl group having 1 to 6 carbon atoms as the substituent include methyl group, ethyl group, n-propyl group, sec-propyl group, iso-propyl group, n-butyl group, tert-butyl group, sec-butyl group, iso-butyl group, n-pentyl group, sec-pentyl group, iso-pentyl group, n-hexyl group, sec-hexyl group and iso-hexyl group. The existence of the alkyl group having 1 to 6 carbon atoms or the phenyl group can be expected to increase compatibility with a polymer such as polyester and enhance the function of the cyclic carbodiimide compound of the present invention. Further, the effect of suppressing the volatility of the cyclic carbodiimide compound can be expected.

X is a divalent or tetravalent group. When X is divalent, q is 0 and when X is tetravalent, q is 1. X is preferably a divalent group of the following formula (i-1).

(i-1)

In the above formula, n is an integer of 1 to 6. Preferred examples of the group of the formula (i-1) include methylene group, ethylene group, 1,3-propylene group, 1,4-butylene group, 1,5-pentane group and 1,6-hexane group. The carbon not directly bonded to oxygen in the 1,3-propylene group, 1,4-butylene group, 1,5-pentane group or 1,6-hexane group may be substituted by at least one selected from the group consisting of alkyl group having 1 to 6 carbon atoms and phenyl group. Example of the alkyl group having 1 to 6 carbon atoms include methyl group, ethyl group, n-propyl group, sec-propyl group, iso-propyl group, n-butyl group, tert-butyl group, sec-butyl group, iso-butyl group, n-pentyl group, sec-pentyl group, iso-pentyl group, n-hexyl group, sec-hexyl group and iso-hexyl group.

X is preferably a group of the following formula (i-2).

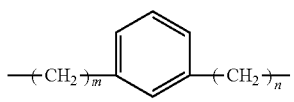

(i-2)

In the above formula, m and n are each independently an integer of 0 to 3. The methylene group of the above formula in which m=0 has a single bond. When X has a 1,3-phenylene group, the stability of the cyclic carbodiimide compound of the present invention is further enhanced and a polymer compound can be advantageously used at a higher process temperature.

X is preferably a group of the following formula (i-3).

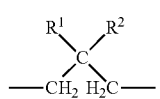

(i-3)

In the above formula, $R^1$ and $R^2$ are each independently an alkyl group having 1 to 6 carbon atoms or phenyl group. Examples of the alkyl group having 1 to 6 carbon atoms include methyl group, ethyl group, n-propyl group, sec-propyl group, iso-propyl group, n-butyl group, tert-butyl group, sec-butyl group, iso-butyl group, n-pentyl group, sec-pentyl group, iso-pentyl group, n-hexyl group, sec-hexyl group and iso-hexyl group.

X is preferably a tetravalent group of the following formula (i-4).

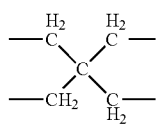

(i-4)

Examples of the cyclic carbodiimide compound of the present invention include a monocyclic compound of the following formula (f) and a bicyclic compound of the following formula (F).

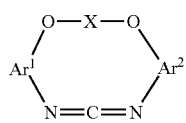

(f)

In the above formula, $Ar^1$, $Ar^2$ and X are as defined in the above formula (i). $Ar^1$ and $Ar^2$ are each preferably an o-phenylene group which may be substituted. The substituent is preferably an alkyl group having 1 to 6 carbon atoms or phenyl group. X is a divalent group.

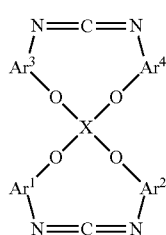

(F)

In the above formula, $Ar^1$ to $Ar^4$ and X are as defined in the formula (i). $Ar^1$ to $Ar^4$ are each preferably an o-phenylene group which may be substituted. The substituent is preferably an alkyl group having 1 to 6 carbon atoms or phenyl group. X is a tetravalent group.

Preferably, the cyclic carbodiimide compound of the present invention has two o-phenylene groups bonded to the 1-position and 3-position of a carbodiimide group, ether oxygen at the ortho-position of the carbodiimide group in the o-phenylene groups and forms acyclic structure in which the ether oxygen atoms are interconnected by X.

That is, a compound represented by the following formula is preferred.

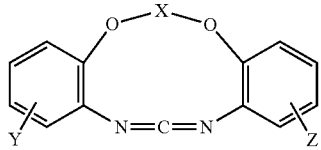
(ii)

In the above formula, X is as defined in the above formula (i). Y and Z are each independently a hydrogen atom, alkyl group having 1 to 6 carbon atoms or phenyl group. Examples of the alkyl group having 1 to 6 carbon atoms include methyl group, ethyl group, n-propyl group, sec-propyl group, iso-propyl group, n-butyl group, tert-butyl group, sec-butyl group, iso-butyl group, n-pentyl group, sec-pentyl group, iso-pentyl group, n-hexyl group, sec-hexyl group and iso-hexyl group.

The following compounds are enumerated as examples of the cyclic carbodiimide compound of the present invention.

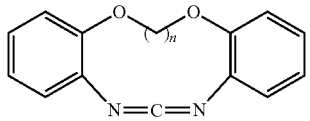

(n is an integer of 1 to 6.)

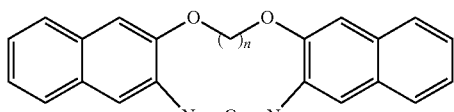

(n is an integer of 1 to 6.)

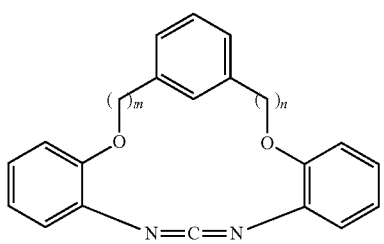

(m is an integer of 0 to 3, and n is an integer of 0 to 3.)

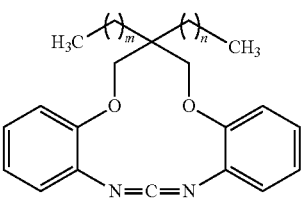

(m is an integer of 0 to 5, and n is an integer of 0 to 5.)

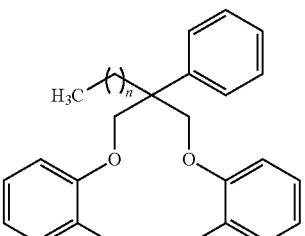

(n is an integer of 0 to 5.)

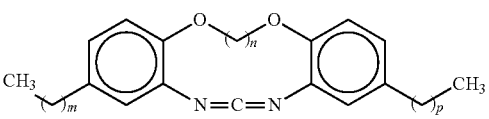

(m and p are each an integer of 1 to 5, and n is an integer of 1 to 6.)

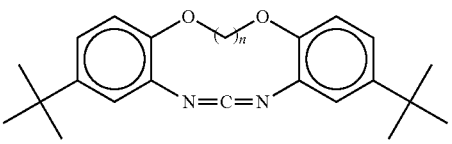

(n is an integer of 1 to 6.)

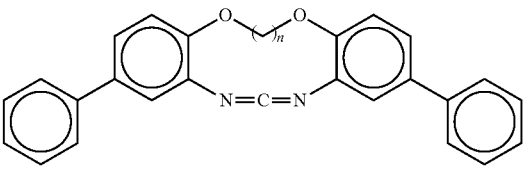

(n is an integer of 1 to 6.)

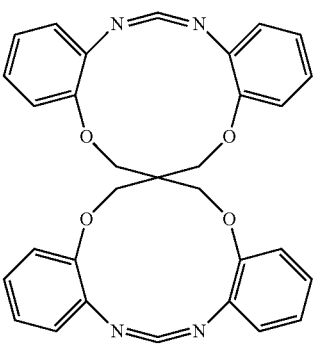 [SMILES: C1=Nc2ccccc2OCC2(COc3ccccc3N=1)COc1ccccc1N=C=Nc1ccccc1OC2]

The molecular weight of the cyclic carbodiimide compound of the present invention is preferably 100 to 1,000. When the molecular weight is lower than 100, the structural stability and volatility of the cyclic carbodiimide compound may become problematic. When the molecular weight is higher than 1,000, synthesis in a dilution system is required for the production of the cyclic carbodiimide, or the yield lowers, thereby causing a cost problem. From this point of view, the molecular weight of the cyclic carbodiimide compound is more preferably 100 to 750, much more preferably 250 to 750. The cyclic carbodiimide compound of the present invention has one carbodiimide group in one ring. When it has two or more carbodiimide groups in one ring, an isocyanate compound is produced by an end-sealing reaction, thereby causing a bad smell.

<Production of Monocyclic Carbodiimide Compound (f)>

The monocyclic carbodiimide compound (f) of the present invention can be produced through the following steps (1) to (4).

The step (1) is to obtain a nitro compound (c). The step (1) has step (1a) and step (1b). The step (2) is to obtain an amide compound (d) from the nitro compound (c). The step (3) and the step (4) are to obtain a monocyclic carbodiimide compound (f) from the amide compound (d). The step (3) to (4) has the embodiment of step (3a) through step (4a), and step (3b) through step (4b).

Stated more specifically, the carbodiimide compound (f) can be produced through the following schemes.
(scheme 1) step (1a)-step (2a)-step (3a)-step (4a)
(scheme 2) step (1a)-step (2a)-step (3b)-step (4b)
(scheme 3) step (1b)-step (2a)-step (3b)-step (4b)
(scheme 4) step (1b)-step (2a)-step (3a)-step (4a)

(Step (1a))

The step (1a) is to obtain the nitro compound (c) of the following formula by reacting a compound of the following formula (a-1), a compound of the following formula (a-2) and a compound of the following formula (b-1).

  (a-1)

  (a-2)

$E^1\text{-}X\text{-}E^2$  (b-1)

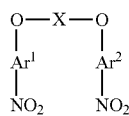  (c)

In the above formulas, X, $Ar^1$ and $Ar^2$ are as defined in the above formula (i). X is a divalent group.

$E^1$ and $E^2$ are each independently a group selected from the group consisting of halogen atom, toluenesulfonyloxy group, methanesulfonyloxy group, benzenesulfonyloxy group and p-bromobenzenesulfonyloxy group. Examples of the halogen atom include chlorine atom, bromine atom and iodine atom.

A conventionally known ether synthesizing method may be used for the reaction. For example, a Williamson's reaction in which a compound of the formula (a-1), a compound of the formula (a-2) and a compound of the formula (b-1) are reacted in a solvent in the presence of a basic compound may be used.

Sodium hydride, metal sodium, sodium hydroxide, potassium hydroxide or potassium carbonate is used as the basic compound. N,N-dimethylformamide, N-methyl-2-pyrrolidone or tetrahydrofuran is used as the solvent. The reaction temperature is preferably 25 to 150° C. Although the reaction proceeds swiftly under the above conditions, a phase-transfer catalyst may be added to promote the reaction.

(Step (1b))

The step (1b) is to obtain the nitro compound of the following formula (c) by reacting a compound of the following formula (a-i), a compound of the following formula (a-ii) and a compound of the following formula (b-i).

  (a-i)

  (a-ii)

$HO\text{---}X\text{---}OH$  (b-i)

  (c)

In the above formulas, $Ar^1$, $Ar^2$ and X are as defined in the above formula (i). X is a divalent group. $E^3$ and $E^4$ are each independently a group selected from the group consisting of halogen atom, toluenesulfonyloxy group, methanesulfonyloxy group, benzenesulfonyloxy group and p-bromobenzenesulfonyloxy group.

A conventionally known ether synthesizing method may be used for the reaction. For example, a Williamson's reaction in which a compound of the formula (a-i), a compound of the formula (a-ii) and a compound of the formula (b-i) are reacted in a solvent in the presence of a basic compound may be used.

Sodium hydride, metal sodium, sodium hydroxide, potassium hydroxide or potassium carbonate is used as the basic compound. N,N-dimethylformamide, N-methyl-2-pyrrolidone or tetrahydrofuran is used as the solvent. The reaction temperature is preferably 25 to 150° C. Although the reaction proceeds swiftly under the above conditions, a phase-transfer catalyst may be added to promote the reaction. A tetrabutylammonium salt, trioctylmethylammonium salt, benzyldimethyloctadecylammonium salt or crown ether is used as the phase-transfer catalyst.

(Step (2))

The step (2) is to obtain the amine compound (d) of the following formula by reducing the obtained nitro compound (c).

  (d)

$Ar^1$, $Ar^2$ and X are as defined in the above formula (i). X is a divalent group.

A conventionally known method may be used for the reaction. For example, the nitro compound (c) is catalytic reduced in a solvent in the presence of hydrogen and a catalyst.

Palladium carbon, palladium carbon-ethylenediamine composite, palladium-fibroin, palladium-polyethyleneimine, nickel or copper is used as the catalyst. Methanol, ethanol, isopropyl alcohol, dioxane, tetrahydrofuran, ethyl acetate, dichloromethane, chloroform or N,N-dimethylformamide is used as the solvent. The reaction temperature is preferably 25 to 100° C. Although the reaction proceeds at normal pressure, pressure is preferably applied to promote the reaction.

As for the reaction for obtaining the amine compound (d), the nitro compound (c) may be reacted with an acid and a metal, or the nitro compound (c) may be reacted with hydrazine and a catalyst.

(Step (3a))

The step (3a) is to obtain a triphenylphosphine compound (e-1) of the following formula by reacting the obtained amine compound (d) with triphenylphosphine dibromide.

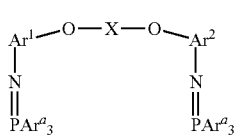
(e-1)

In the above formula, $Ar^1$, $Ar^2$ and X are as defined in the above formula (i). $Ar^a$ is a phenyl group.

A conventionally known method may be used for the reaction. For example, the amine compound of the formula (d) is reacted with triphenylphosphine dibromide in a solvent in the presence of a basic compound. Triethylamine or pyridine is used as the basic compound. Dichloroethane, chloroform or benzene is used as the solvent. The reaction temperature is preferably 0 to 80° C.

(Step (4a))

The step (4a) is to obtain a cyclic carbodiimide compound (f) by isocyanating the obtained triphenylphosphine compound in a reaction system and then decarbonating the isocyanated product directly.

A conventionally known method may be used for the reaction. For example, the triphenylphosphine compound of the formula (e-1) is reacted in a solvent in the presence of di-tert-butyl dicarbonate and N,N-dimethyl-4-aminopyridine. Dichloromethane or chloroform is used as the solvent. The reaction temperature is preferably 10 to 40° C.

(Step (3b))

The step (3b) is to obtain an urea compound or thiourea compound of the following formula (e-2) by reacting the amine compound (d) with carbon dioxide or carbon disulfide.

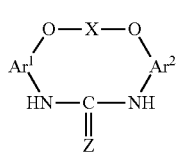
(e-2)

In the above formula, $Ar^1$, $Ar^2$ and X are as defined in the above formula (i), and Z is an oxygen atom or sulfur atom.

A conventionally known method may be used for the reaction for obtaining the urea compound (e-2). For example, the amine compound (d) is reacted in a solvent in the presence of carbon dioxide, a phosphorus compound and a basic compound.

A phosphorous acid ester or a phosphonic acid ester is used as the phosphorus compound. Triethylamine, pyridine, imidazole or picoline is used as the basic compound. Pyridine, N,N-dimethylformamide, acetonitrile, chlorobenzene or toluene is used as the solvent. The reaction temperature is preferably 0 to 80° C.

As another reaction for obtaining the urea compound (e-2), the amine compound (d) is reacted with carbon monoxide, or the amine compound (d) is reacted with phosgene.

A conventionally known method may be used for the reaction for obtaining the thiourea compound (e-2). For example, the amine compound (d) is reacted in a solvent in the presence of carbon disulfide and a basic compound.

Triethylamine, pyridine, imidazole or picoline is used as the basic compound. Acetone, methanol, ethanol, isopropyl alcohol, 2-butanone, pyridine, N,N-dimethylformamide or acetonitrile is used as the solvent. The reaction temperature is preferably 25 to 90° C. Although the reaction proceeds swiftly under the above conditions, carbon tetrabromide may be used to promote the reaction.

(Step (4b))

The step (4b) is to obtain the cyclic carbodiimide compound (f) by dehydrating the obtained urea compound (e-2) or desulfurizing the thiourea compound (e-2).

A conventionally known method may be used for the reaction. For example, the urea or thiourea compound (e-2) is reacted in a solvent in the presence of toluenesulfonyl chloride or methylsulfonyl chloride to dehydrate the urea compound (e-2) or desulfurize the thiourea compound (e-2).

Dichloromethane, chloroform or pyridine is used as the solvent. The reaction temperature is preferably 0 to 80° C.

As another reaction for obtaining the cyclic carbodiimide compound (f), the urea compound (e-2) is reacted with mercury oxide, or the thiourea compound (e-2) is reacted with sodium hypochlorite.

<Production of Bicyclic Carbodiimide Compound (f)>

The bicyclic carbodiimide compound (F) of the present invention can be produced through the following steps (1) to (4).

The step (1) is to obtain a nitro compound (C). The step (1) has step (1A) and step (1B). The step (2) is to obtain an amide compound (D) from the nitro compound (C). The step (3) and the step (4) are to obtain the bicyclic carbodiimide compound (F) from the amide compound (D). The step (3) to (4) has the embodiment of step (3A) through step (4A), and step (3B) through step (4B).

The carbodiimide compound (F) can be produced through the following schemes.
(scheme 1) step (1A)-step (2A)-step (3A)-step (4A)
(scheme 2) step (1A)-step (2A)-step (3B)-step (4B)
(scheme 3) step (1B)-step (2A)-step (3B)-step (4B)
(scheme 4) step (1B)-step (2A)-step (3A)-step (4A)

(Step (1A))

The step (1A) is to obtain a nitro compound of the following formula (C) by reacting compounds of the following formulas (A-1) to (A-4) and a compound of the following formula (B-1).

 (A-1)

 (A-2)

 (A-3)

 (A-4)

 (B-1)

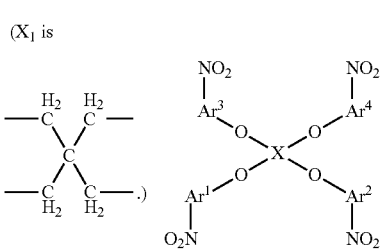

(C)

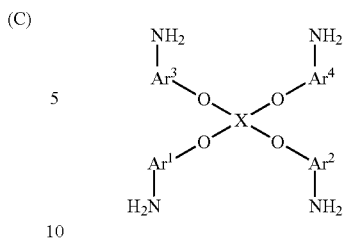

In the above formulas, $Ar^1$ to $Ar^4$ and X are as defined in the formula (i). X is a tetravalent group. $E^1$ to $E^4$ are each independently a group selected from the group consisting of halogen atom, toluenesulfonyloxy group, methanesulfonyloxy group, benzenesulfonyloxy group and p-bromobenzenesulfonyloxy group.

The reaction conditions are the same as those in the above step (1a).

(Step (1B))

The step (1B) is to obtain the nitro compound of the following formula (C) by reacting compounds of the following formulas (A-i) to (A-iv) and a compound of the following formula (B-1).

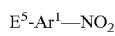 (A-i)

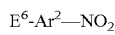 (A-ii)

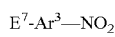 (A-iii)

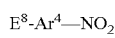 (A-iv)

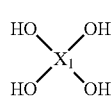 (B-i)

(C)

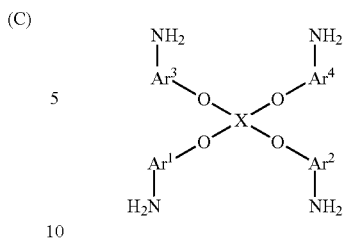

In the above formulas, $Ar^1$ to $Ar^4$ and X are as defined in the formula (i). $E^5$ to $E^8$ are each independently a group selected from the group consisting of halogen atom, toluenesulfonyloxy group, methanesulfonyloxy group, benzenesulfonyloxy group and p-bromobenzenesulfonyloxy group.

The reaction conditions are the same as those in the above step (1b).

(Step (2A))

The step (2A) is to obtain the amine compound (D) of the following formula by reducing the obtained nitro compound.

(D)

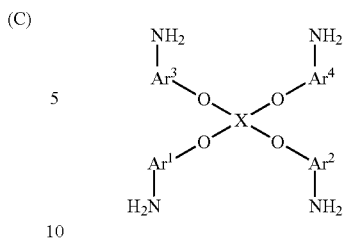

$Ar^1$ to $Ar^4$ and X are as defined in the formula (i). The reaction conditions are the same as those in the above step (2a).

(Step (3A))

The step (3A) is to obtain a triphenylphosphine compound (E-1) of the following formula by reacting the obtained amine compound (D) with triphenylphosphine dibromide.

(E-1)

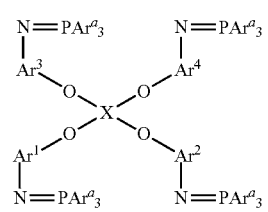

In the above formula, $Ar^1$ to $Ar^4$ and X are as defined in the formula (i), and $Ar^a$ is a phenyl group. The reaction conditions are the same as those in the above step (3a).

(Step (4A))

The step (4A) is to obtain the compound (F) of the following formula by isocyanating the obtained triphenylphosphine compound in a reaction system and then decarbonating the isocyanated product directly.

(F)

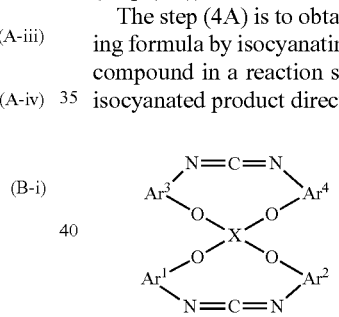

In the above formula, $Ar^1$ to $Ar^4$ and X are as defined in the formula (i). The reaction conditions are the same as those in the above step (4a).

(Step (3B))

The step (3B) is to obtain a urea or thiourea compound (E-2) of the following formula by reacting the amine compound with carbon dioxide or carbon disulfide.

(E-2)

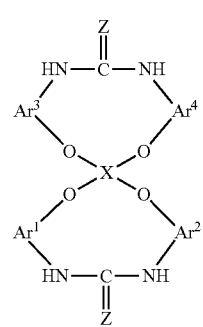

In the above formula, $Ar^1$ to $Ar^4$ and X are as defined in the formula (i), and Z is an oxygen atom or sulfur atom.

The reaction conditions are the same as those in the above step (3b).

(Step (4B))

The step (4B) is to obtain the compound (F) of the following formula by dehydrating the obtained urea compound or desulfurizing the thiourea compound.

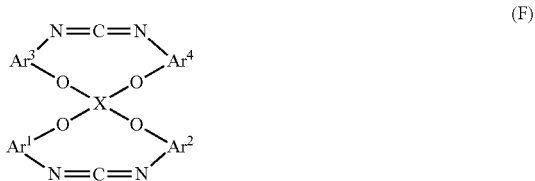

(F)

In the above formula, $Ar^1$ to $Ar^4$ and X are as defined in the formula (i).

The reaction conditions are the same as those in the above step (4b).

(Other Production Processes)

The cyclic carbodiimide compound of the present invention can be produced by conventionally known processes besides the above production process. For example, it is produced from an amine compound through an isocyanate compound, from an amine compound through an isocyanate compound or from a carboxylic acid compound through an isocyanate compound.

The cyclic carbodiimide compound effectively can seal the acid group of a polymer compound. A conventionally known sealing agent for the carboxyl group of a polymer may be optionally used in combination as long as it does not work against the subject matter of the present invention. As the conventionally known carboxyl group sealing agent, agents disclosed by JP-A 2005-2174 such as epoxy compounds, oxazoline compounds and oxazine compounds may be used.

<Polymer Compound>

In the present invention, the polymer compound for which the cyclic carbodiimide compound is used has an acid group. The acid group is at least one selected from the group consisting of carboxyl group, sulfonate group, sulfinate group, phosphonate group and phosphinate group. The polymer compound is at least one selected from the group consisting of polyester, polyamide, polyamide-imide, polyimide and polyester amide.

The polyester is, for example, a polymer or copolymer obtained by polycondensing at least one selected from a dicarboxylic acid or ester forming derivative thereof with a diol or ester forming derivative thereof, a hydroxycarboxylic acid or ester forming derivative thereof, or a lactone, preferably a thermoplastic polyester resin. The thermoplastic polyester resin may contain a crosslinked structure treated with a radical generation source such as energy active line or an oxidizing agent to achieve moldability.

Examples of the above dicarboxylic acid or ester forming derivative thereof include aromatic dicarboxylic acids and ester forming derivatives thereof such as terephthalic acid, isophthalic acid, phthalic acid, 2,6-naphthalenedicarboxylic acid, 1,5-naphthalenedicarboxylic acid, bis(p-carboxyphenyl)methane, anthracenedicarboxylic acid, 4,4'-diphenyl ether dicarboxylic acid, 5-tetrabutylphosphonium isophthalic acid and 5-sodium sulfoisophthalic acid. Aliphatic dicarboxylic acids such as oxalic acid, succinic acid, adipic acid, sebacic acid, azelaic acid, dodecanedioic acid, malonic acid, glutaric acid and dimeric acid and ester forming derivatives thereof are also included. Alicyclic dicarboxylic acids such as 1,3-cyclohexanedicarboxylic acid and 1,4-cyclohexanedicarboxylic acid and ester forming derivatives thereof are further included.

Examples of the above diol or ester forming derivative thereof include aliphatic glycols having 2 to 20 carbon atoms such as ethylene glycol, propylene glycol, 1,3-propanediol, 1,4-butanediol, neopentyl glycol, 1,5-pentanediol, 1,6-hexanediol, decamethylene glycol, cyclohexanedimethanol, cyclohexanediol and dimer diol. Long-chain glycols having a molecular weight of 200 to 100,000, that is, polyethylene glycol, polytrimethylene glycol, poly-1,2-propylene glycol and polytetramethylene glycol are also included. Aromatic dioxy compounds, that is, 4,4'-dihydroxybiphenyl, hydroquinone, tert-butyl hydroquinone, bisphenol A, bisphenol S and bisphenol F and ester forming derivatives thereof are further included.

Examples of the above hydroxycarboxylic acid include glycolic acid, lactic acid, hydroxypropionic acid, hydroxybutyric acid, hydroxyvaleric acid, hydroxycaproic acid, hydroxybenzoic acid, p-hydroxybenzoic acid, 6-hydroxy-2-naphthoic acid and ester forming derivatives thereof. Examples of the above lactone include caprolactone, valerolactone, propiolactone, undecalactone and 1,5-oxepan-2-one.

Aromatic polyesters obtained by polycondensing an aromatic dicarboxylic acid or ester forming derivative thereof and an aliphatic diol or ester forming derivative thereof as the main ingredients include polymers obtained by polycondensing an aromatic carboxylic acid or ester forming derivative thereof, preferably terephthalic acid or naphthalene-2,6-dicarboxylic acid or ester forming derivative thereof and an aliphatic diol selected from ethylene glycol, 1,3-propaneidol and butanediol or ester forming derivative thereof as the main ingredients.

Preferred specific examples of the aromatic polyesters include polyethylene terephthalate, polyethylene naphthalate, polytrimethylene terephthalate, polytrimethylene naphthalate, polybutylene terephthalate, polybutylene naphthalate, polyethylene (terephthalate/isophthalate), polytrimethylene (terephthalate/isophthalate), polybutylene (terephthalate/isophthalate), polyethylene terephthalate-.polyethylene glycol, polytrimethylene terephthalate.polyethylene glycol, polybutylene terephthalate.polyethylene glycol, polybutylene naphthalate.polyethylene glycol, polyethylene terephthalate.poly(tetramethyleneoxide)glycol, polytrimethylene terephthalate.poly(tetramethyleneoxide) glycol, polybutylene terephthalate.poly(tetramethyleneoxide)glycol, polybutylene naphthalate.poly(tetramethyleneoxide)glycol, polyethylene (terephthalate/isophthalate).poly(tetramethyleneoxide)glycol, polytrimethylene (terephthalate/isophthalate).poly(tetramethyleneoxide) glycol, polybutylene (terephthalate/isophthalate).poly(tetramethyleneoxide)glycol, polybutylene (terephthalate/succinate), polyethylene(terephthalate/succinate), polybutylene (terephthalate/adipate) and polyethylene (terephthalate/adipate).

Aliphatic polyesters include polymers comprising an aliphatic hydroxycarboxylic acid as the main constituent component, polymers obtained by polycondensing an aliphatic polycarboxylic acid or ester forming derivative thereof and an aliphatic polyhydric alcohol as the main ingredients, and copolymers thereof.

The polymers comprising an aliphatic hydroxycarboxylic acid as the main constituent component include polycondensates such as glycolic acid, lactic acid, hydroxypropionic acid, hydroxybutyric acid, hydroxyvaleric acid and hydroxycaproic acid, and copolymers thereof. Out of these, polyglycolic acid, polylactic acid, poly(3-hydroxycarbonbutyric acid), poly(4-polyhydroxybutyric acid), poly(3-hydroxyhexanoic acid), polycaprolactone and copolymers thereof are preferably used. Poly(L-lactic acid), poly(D-lactic acid), stereocomplex polylactic acid and racemic polylactic acid are particularly preferably used.

Polymers comprising an aliphatic polycarboxylic acid and an aliphatic polyhydric alcohol as the main constituent components are also used as the polyester. Examples of the polycarboxylic acid include aliphatic dicarboxylic acids such as oxalic acid, succinic acid, adipic acid, sebacic acid, azelaic acid, dodecanedioic acid, malonic acid, glutaric acid and dimeric acid. Alicyclic dicarboxylic acid units such as 1,3-cyclohexanedicarboxylic acid and 1,4-cyclohexanedicarboxylic acid and ester forming derivatives thereof are also included.

Examples of the diol component include aliphatic glycols having 2 to 20 carbon atoms such as ethylene glycol, 1,3-propanediol, 1,4-butanediol, neopentyl glycol, 1,5-pentanediol, 1,6-hexanediol, decamethylene glycol, cyclohexanedimethanol, cyclohexanediol and dimer diol. Long-chain glycols having a molecular weight of 200 to 100,000, that is, condensates comprising polyethylene glycol, polytrimethylene glycol, poly(1,2-propylene glycol) or polytetramethylene glycol as the main constituent component are also included. More specifically, they include polyethylene adipate, polyethylene succinate, polybutylene adipate and polybutylene succinate and copolymers thereof.

Further, wholly aromatic polyesters include polymers obtained by polycondensing an aromatic carboxylic acid or ester forming derivative thereof, preferably terephthalic acid, naphthalene-2,6-dicarboxylic acid or ester forming derivative thereof and an aromatic polyhydroxy compound or ester forming derivative thereof as the main ingredients.

More specifically, poly(4-oxyphenylene-2,2-propylidene-4-oxyphenylene-terephthaloyl-co-isophthaloyl) is such an example.

These polyesters contain 1 to 50 eq/ton of a carboxyl group and/or a hydroxyl group as a carbodiimide reactive component at a terminal of the molecule. Since these terminal groups, especially the carboxyl group reduces the stability of a polyester, it is preferably sealed with a cyclic carbodiimide compound.

When the carboxyl terminal group is sealed with a carbodiimide compound, it can be sealed without producing a toxic free isocyanate by using the cyclic carbodiimide compound of the present invention.

Further, as an additional effect, the increase of the molecular weight or the restrain of reduction of the molecular weight of a polyester by the chain extension function of an isocyanate terminal group formed in the polyester which is not liberated when the terminal group is sealed with the cyclic carbodiimide compound and a hydroxyl terminal group or carboxyl terminal group existent in the polyester can be suppressed more efficiently as compared with a conventional linear carbodiimide compound. This is of great industrial significance.

The above polyesters can be produced by known methods (for example, methods described in the saturated polyester resin handbook (written by Kazuo Yuki, published by Nikkan Kogyo Shimbun on Dec. 22, 1989).

Further, examples of the polyester in the present invention include unsaturated polyester resins obtained by copolymerizing an unsaturated polycarboxylic acid or ester forming derivative thereof, and polyester elastomers containing a low-melting polymer segment besides the above polyesters.

Examples of the unsaturated polycarboxylic acid include maleic anhydride, tetrahydromaleic anhydride, fumaric acid and endomethylene tetrahydromaleic anhydride. Monomers are added to the unsaturated polyester to control its curing properties, and the unsaturated polyester is cured by heat, radical, light, or active energy line such as electron beam and molded. For the unsaturated resin, the control of the carboxyl group is an important technical matter with respect to rheologic characteristics such as thixotropy and resin durability. However, advantages that the carboxyl group can be sealed and controlled by the cyclic carbodiimide compound without producing a toxic free isocyanate and that the molecular weight of the unsaturated resin can be increased effectively by the cyclic carbodiimide compound are of great industrial significance.

Further, in the present invention, the polyester may be a polyester elastomer obtained by copolymerizing a soft component. The polyester elastomer is a copolymer comprising a high-melting polyester segment and a low-melting polymer segment having a molecular weight of 400 to 6,000 as described in publicly known documents, for example, JP-A 11-92636.

The melting point of a copolymer composed of a high-melting polyester segment alone is 150° C. or higher. The melting point or softening point of a copolymer composed of a low-melting polymer segment alone is 80° C. or lower. The low-melting polymer segment is preferably composed of a polyalkylene glycol or an aliphatic dicarboxylic acid having 2 to 12 carbon atoms and an aliphatic glycol having 2 to 10 carbon atoms. Although the elastomer has a problem with hydrolytic stability, the significance of being able to control its carboxyl group by the cyclic carbodiimide compound and the industrial significance of being able to suppress the reduction of its molecular weight or increase its molecular weight without any safety problem by the cyclic carbodiimide compound are great.

The polyamide is a thermoplastic polymer having an amide bond obtained mainly from amino acid, lactam or diamine and dicarboxylic acid or amide forming derivative thereof.

In the present invention, a polycondensate obtained by condensing a diamide and a dicarboxylic acid or acyl active form, a polymer obtained by polycondensing an aminocarboxylic acid or lactam, or amino acid, or a copolymer thereof may be used as the polyamide.

The diamine is selected from an aliphatic diamine and an aromatic diamine. Examples of the aliphatic diamine include tetramethylenediamine, hexamethylenediamine, undecamethylenediamine, dodecamethylenediamine, 2,2,4-trimethylhexamethylenediamine, 2,4,4-trimethylhexamethylenediamine, 5-methylnonamethylenediamine, 2,4-dimethyloctamethylenediamine, metaxylylenediamine, paraxylylenediamine, 1,3-bis(aminomethyl)cyclohexane, 1-amino-3-aminomethyl-3,5,5-trimethylcyclohexane, 3,8-bis(aminomethyl)tricyclodecane, bis(4-aminocyclohexyl)methane, bis(3-methyl-4-aminocyclohexyl)methane, 2,2-bis(4-aminocyclohexyl)propane, bis(aminopropyl)piperazine and aminoethylpiperazine.

Examples of the aromatic diamine include p-phenylenediamine, m-phenylenediamine, 2,6-naphthalenediamine, 4,4'-diphenyldiamine, 3,4'-diphenyldiamine, 4,4'-diaminodiphenyl ether, 3,4'-diaminodiphenyl ether, 4,4'-diaminodiphenyl sulfone, 3,4'-diaminodiphenyl sulfone, 4,4'-diaminodiphenyl ketone, 3,4'-diaminodiphenyl ketone and 2,2-bis(4-aminophenyl)propane.

Examples of the dicarboxylic acid include adipic acid, suberic acid, azelaic acid, sebacic acid, dodecanoic acid, terephthalic acid, isophthalic acid, naphthalenedicarboxylic acid, 2-chloroterephthalic acid, 2-methylterephthalic acid, 5-methylisophthalic acid, 5-sodium sulfoisophthalic acid, hexahydroterephthalic acid, hexahydroisophthalic acid and diglycolic acid. Specific examples of the polyamide include aliphatic polyamides such as polycapramide (nylon 6), polytetramethylene adipamide (nylon 46), polyhexamethylene adipamide (nylon 66), polyhexamethylene sebacamide (nylon 610), polyhexamethylene dodecamide (nylon 612), polyundecamethylene adipamide (nylon 116), polyundecaneamide (nylon 11) and polydodecaneamide (nylon 12).

Aliphatic-aromatic polyamides such as polytrimethyl hexamethylene terephthalamide, polyhexamethylene isophthalamide (nylon 6I), polyhexamethylene terephthal/isophthalamide (nylon 6T/6I), polybis(4-aminocyclohexyl) methane dodecamide (nylon PACM12), polybis(3-methyl-4-aminocyclohexyl)methane dodecamide (nylon dimethyl PACM12), polymetaxylylene adipamide (nylon MXD6), polyundecamethylene terephthalamide (nylon 11T), polyundecamethylene hexahydroterephthalamide (nylon 11T(H)) and copolyamides thereof, and copolymers and mixtures thereof are also included. Poly(p-phenylene terephthalamide) and poly(p-phenylene terephthalamide-co-isophthalamide) are further included.

Examples of the amino acid include ω-aminocaproic acid, ω-aminoenanthic acid, ω-aminocaprylic acid, ω-aminopelargonic acid, ω-aminocapric acid, 11-aminoundecanoic acid, 12-aminododecanoic acid and paraminomethylbenzoic acid, and examples of the lactam include ω-caprolactam, ω-enantholactam, ω-capryllactam and ω-laurolactam.

The molecular weights of these polyamide resins are not particularly limited but the relative viscosity measured at 25° C. in a 98% concentrated sulfuric acid solution containing 1 wt % of the polyamide resin is preferably 2.0 to 4.0.

These amide resins may be produced by well known methods, for example, methods described in the polyamide resin handbook (written by Osamu Fukumoto and published by Nikkan Kogyo Shimbun on Jan. 30, 1988).

Further, the polyamide of the present invention includes a polyamide known as a polyamide elastomer. The polyamide is a graft or block copolymer obtained by reacting a polyamide forming component having 6 or more carbon atoms with a poly(alkyleneoxide)glycol. The bond between the polyamide forming component having 6 or more carbon atoms and the poly(alkyleneoxide)glycol component is generally an ester bond or an amide bond but not limited to these, and a third component such as dicarboxylic acid or diamine may be used as a reaction component for these components.

Examples of the poly(alkyleneoxide)glycol include polyethylene oxide glycol, poly(1,2-propyleneoxide)glycol, poly (1,3-proypleneoxide)glycol, poly(tetramethyleneoxide)glycol, poly(hexamethyleneoxide)glycol, block or random copolymer of ethylene oxide and propylene oxide, and block or random copolymer of ethylene oxide and tetrahydrofuran. The number average molecular weight of the poly(alkyleneoxide)glycol is preferably 200 to 6,000, more preferably 300 to 4,000 from the viewpoints of polymerizability and stiffness. The polyamide elastomer used in the present invention is preferably a polyamide elastomer obtained by polymerizing caprolactam, polyethylene glycol or terephthalic acid.

Although the polyamide resin contains 30 to 100 eq/ton of a carboxyl group and 30 to 100 eq/ton of an amino group as easily understood from its raw materials, it is known that the carboxyl group has an unfavorable effect on the stability of the polyamide.

The significance of a composition whose carboxyl group content is reduced to not more than 20 eq/ton, preferably not more than 10 eq/ton, more preferably not more than that without causing a safety problem and whose molecular weight reduction is suppressed more effectively by the cyclic carbodiimide compound of the present invention is great.

The polyamide-imide resin used in the present invention has a main recurring structural unit represented by the following formula (I).

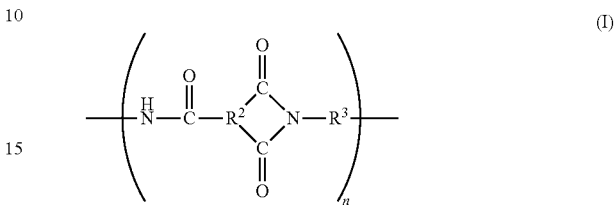

In the above formula, $R^2$ is a tervalent organic group, $R^3$ is a divalent organic group, and n is a positive integer.

Typical methods of synthesizing this polyamide-imide resin include (1) one in which a diisocyanate and a tribasic acid anhydride are reacted with each other, (2) one in which a diamine and a tribasic acid anhydride are reacted with each other, and (3) one in which a diamine and a tribasic acid anhydride chloride are reacted with each other. The method of synthesizing the polyamide-imide resin used in the present invention is not limited to these. Typical compounds used in the above synthesizing methods are listed below.

Preferred examples of the diisocyanate include 4,4'-diphenylmethane diisocyanate, xylylene diisocyanate, 3,3'-diphenylmethane diisocyanate, 4,4'-diphenyl ether diisocyanate, 3,3'-diphenyl ether diisocyanate and paraphenylene diisocyanate.

Preferred examples of the diamine include 4,4'-diaminodiphenylsulfone, 3,3'-diaminodiphenylsulfone, 4,4'-diaminodiphenyl ether, 3,3'-diaminodiphenyl ether, 4,4'-diaminodiphenyl methane, 3,3'-diaminodiphenyl methane, xylylenediamine and phenylenediamine. Out of these, 4,4'-diphenylmethane diisocyanate, 3,3'-diphenylmethane diisocyanate, 4,4'-diphenyl ether diisocyanate, 3,3'-diphenyl ether diisocyanate, 4,4'-diaminodiphenyl ether, 3,3'-diaminodiphenyl ether, 4,4'-diaminodiphenyl methane and 3,3'-diaminodiphenyl methane are more preferred.

The tribasic acid anhydride is preferably trimellitic anhydride, and the tribasic acid anhydride chloride is preferably trimellitic anhydride chloride.

To synthesize the polyamide-imide resin, a dicarboxylic acid or a tetracarboxylic dianhydride can be reacted simultaneously as long as the characteristic properties of the polyamide-imide resin are not impaired. Examples of the dicarboxylic acid include terephthalic acid, isophthalic acid and adipic acid. Examples of the tetracarboxylic dianhydride include pyromellitic dianhydride, benzophenone tetracarboxylic dianhydride and biphenyl tetracarboxylic dianhydride. They are preferably used in an amount of not more than 50% by equivalent based on the total of all the acid components.

Since the durability of the polyamide-imide resin may be reduced by the concentration of the carboxyl group contained in the polymer, the concentration of the carboxyl group is preferably reduced to 1 to 10 eq/ton or below this range. In the cyclic carbodiimide compound of the present invention, the content of the carboxyl group can be advantageously reduced to the above range.

A thermoplastic polyimide resin is preferably selected as the polyimide resin. An example of the polyimide resin is a polyimide comprising the following diamine component and a tetracarboxylic acid.

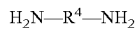

(in the above formula, $R^4$ is (i) a single bond, (ii) an aliphatic hydrocarbon group having 2 to 12 carbon atoms, (iii) an alicyclic group having 4 to 30 carbon atoms, (iv) an aromatic group having 6 to 30 carbon atoms, (v) -Ph-O—$R^5$—O-Ph- ($R^5$ is a phenylene group or Ph-$W^1$-Ph-, $W^1$ is a single bond, alkylene group having 1 to 4 carbon atoms which may be substituted by a halogen atom, —O-Ph-O, —O—, —CO—, —S—, —SO— or —$SO_2$—), or (vi) —$R^6$—$(SiR^7{}_2O)_m$—$SiR^7{}_2$—$R^6$— ($R^6$ is —$(CH_2)_s$—, —$(CH_2)_s$-Ph-, —$(CH_2)_s$—O-Ph- or Ph-, m is an integer of 1 to 100, s is an integer of 1 to 4, and $R^7$ is an alkyl group having 1 to 6 carbon atoms, phenyl group or alkylphenyl group having 1 to 6 carbon atoms.)

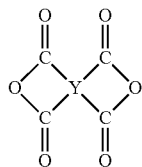

[In the above formula, Y is a tetravalent aliphatic group having 2 to 12 carbon atoms, tetravalent alicyclic group having 4 to 8 carbon atoms, tetravalent aromatic group of a mono- or polycondensed ring having 6 to 14 carbon atoms, >Ph-$W^2$-Ph< ($W^2$ is a single bond, alkylene group having 1 to 4 carbon atoms which may be substituted by a halogen atom, —O-Ph-O—, —O—, —CO—, —SO— or —$SO_2$—).]

Examples of the tetracarboxylic anhydride used in the production of polyamide acid include pyromellitic anhydride (PMDA), 4,4'-oxydiphthalic anhydride (ODPA), biphenyl-3,3',4,4'-tetracarboxylic anhydride (BPDA), benzophenone 3,3',4,4'-tetracarboxylic anhydride (BTDA), ethylene tetracarboxylic anhydride, butane tetracarboxylic anhydride, cyclopentane tetracarboxylic anhydride, benzophenone-2,2',3,3'-tetracarboxylic anhydride, biphenyl-2,2,3,3'-tetracarboxylic anhydride, anhydrous 2,2-bis(3,4-dicarboxyphenyl) propane, anhydrous 2,2-bis(2,3-dicarboxyphenyl)propane, anhydrous bis(3,4-dicarboxyphenyl)ether, anhydrous bis(3,4-dicarboxyphenyl)sulfone, anhydrous 1,1-bis(2,3-dicarboxyphenyl)ethane, anhydrous bis(2,3-dicarboxyphenyl) methane, anhydrous bis(3,4-dicarboxyphenyl)methane, 4,4'-(P-phenylenedioxy)diphthalic anhydride, 4,4'-(m-phenylenedioxy)diphthalic anhydride, naphthaline-2,3,6,7-tetracarboxylic anhydride, naphthaline-1,4,5,8-tetracarboxylic anhydride, naphthaline-1,2,5,6-tetracarboxylic anhydride, benzene-1,2,3,4-tetracarboxylic anhydride, perylene-3,4,9,10-tetracarboxylic anhydride, anthracene-2,3,6,7-tetracarboxylic anhydride and phenanthrene-1,2,7,8-tetracarboxylic anhydride. The present invention is not limited to these. These dicarboxylic anhydrides may be used alone or in combination of two or more. Out of these, pyromellitic anhydride (PMDA), 4,4'-oxydiphthalic anhydride (ODPA), biphenyl-3,3',4,4'-tetracarboxylic anhydride (BPDA), benzophenone-3,3',4,4'-tetracarboxylic anhydride and biphenylsulfone-3,3',4,4'-tetracarboxylic anhydride (DSDA) are preferably used.

Examples of the diamine used in the production of polyimide include 4,4'-diaminodiphenyl ether, 4,4'-diaminodiphenylmethane, 4,4'-diaminodiphenylsulfone, 4,4'-diaminodiphenyl thioether, 4,4'-di(meta-aminophenoxy) diphenylsulfone, 4,4'-di(para-aminophenoxy) diphenylsulfone, o-phenylenediamine, m-phenylenediamine, p-phenylenediamine, benzidine, 2,2'-diaminobenzophenone, 4,4'-diaminobenzophenone, 4,4'-diaminodiphenyl-2,2'-propane, 1,5-diaminonaphthaline, 1,8-diaminonaphthaline, trimethylenediamine, tetramethylenediamine, hexamethylenediamine, 4,4-dimethylheptamethylenediamine, 2,11-dodecadiamine, di(para-aminophenoxy)dimethylsilane, 1,4-di(3-aminopropyldiaminosilane)benzene, 1,4-diaminocyclohexane, ortho-tolyldiamine, meta-tolyldiamine, acetoguanamine, benzoguanamine, 1,3-bis(3-aminophenoxy)benzene (APB), bis[4-(3-aminophenoxy)phenyl]methane, 1,1-bis[4-(3-aminophenoxy)phenyl]ethane, 1,2-bis[4-(3-aminophenoxy)phenyl]ethane, 2,2-bis[4-(3-aminophenoxy)phenyl]ethane, 2,2-bis[4-(3-aminophenoxy)phenyl]propane, 2,2-bis[4-(3-aminophenoxy)phenyl]butane, 2,2-bis[4-(3-aminophenoxy) phenyl]-1,1,1,3,3,3-hexafluoro propane, 4,4'-di(3-aminophenoxy)biphenyl, di[4-(3-aminophenoxy)phenyl] ketone, di[4-(3-aminophenoxy)phenyl]sulfide, di[4-(3-aminophenoxy)phenyl]sulfoxide, di[4-(3-aminophenoxy) phenyl]sulfone and di(4-(3-amionohpenoxy)phenyl)ether. The present invention is not limited to these. The above diamines may be used alone or in combination.

Examples of the thermoplastic polyimide include polyimide resins comprising a tetracarboxylic anhydride represented by the following formulas and a known diamine such as p-phenylenediamine, cyclohexanediamine or hydrogenated bisphenol A type diamine. Commercially available products of the thermoplastic polyimide include Ultem1000, Ultem1010, UltemCRS5001 and UltemXH6050 of General Electric Co., Ltd. and Auram 250AM of Mitsui Chemical Co., Ltd.

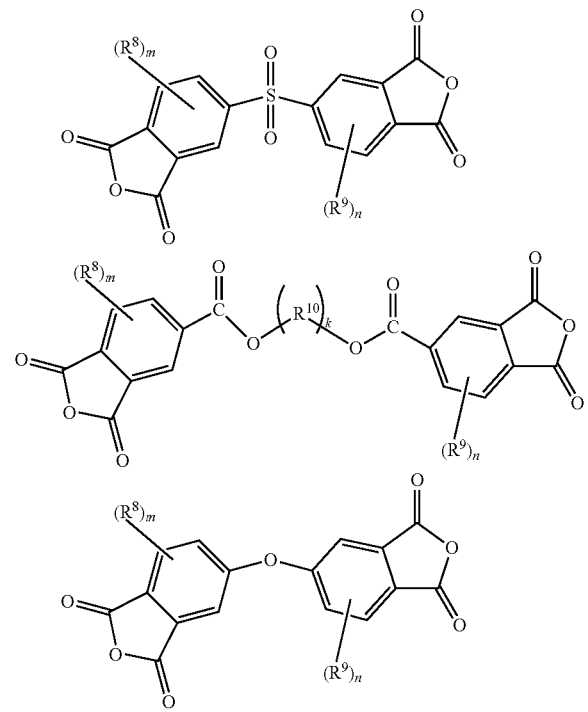

[In the above formulas, $R^8$ and $R^9$ are each independently a hydrogen atom, linear or branched alkyl group having 1 to 10 carbon atoms, or aryl group, $R^{10}$ is an arylene group having 6 to 30 carbon atoms or alkylene group having 2 to 20 carbon atoms, m and n are each an integer of 0 to 5, and k is an integer of 1 to 3.]

Examples of the polyester amide resin include conventionally known polyester amide resins obtained by copolymerizing a polyester constituent component and a polyamide constituent component, out of which thermoplastic polyesteramide resins are preferred.

The polyester amide resin can be synthesized by known methods. For example, the above polyamide constituent component is first subjected to a polycondensation reaction so as to synthesize a polyamide having a functional group at a terminal, and the polyester constituent component is polymerized in the presence of the polyamide. This polycondensation reaction is generally realized by carrying out an amidation reaction as a first stage and an esterification reaction as a second stage. The above polyester constituent components are preferably selected as the polyester constituent component. The above polyamide constituent components are preferably selected as the polyamide constituent component.

<Use of Carbodiimide>

In the present invention, the cyclic carbodiimide compound is mixed with a polymer compound having an acid group and reacted with the compound to seal the acid group. The method of adding and mixing the cyclic carbodiimide compound with the polymer compound is not particularly limited, and a conventionally known method in which the cyclic carbodiimide compound is added as a solution, a melt or a master batch of a polymer, or a method in which a solid polymer compound is brought into contact with a liquid containing the cyclic carbodiimide compound dissolved therein, dispersed therein or molten therein to impregnate the cyclic carbodiimide compound may be employed.

In the case of the method in which the cyclic carbodiimide compound is added as a solution, a melt or a master batch of a polymer, a conventionally known kneader is used to add the cyclic carbodiimide compound. For kneading, the cyclic carbodiimide compound is preferably kneaded in a solution state or a molten state from the viewpoint of uniform kneading. The kneader is not particularly limited, and conventionally known vertical reactors, mixing tanks, kneading tanks or single-screw or multi-screw vertical kneading machines such as a single-screw or multi-screw extruder or kneader may be used. The time during which the cyclic carbodiimide compound is mixed with the polymer compound is not particularly limited and differs according to the mixer and the mixing temperature but preferably 0.1 minute to 2 hours, more preferably 0.2 to 60 minutes, much more preferably 0.2 to 30 minutes.

As the solvent may be used a solvent which is inert to the polymer compound and the cyclic carbodiimide compound. A solvent which has affinity for both of them and dissolves at least part of each of these compounds is preferred.

The solvent is selected from a hydrocarbon-based solvent, ketone-based solvent, ester-based solvent, ether-based solvent, halogen-based solvent and amide-based solvent.

Examples of the hydrocarbon-based solvent include hexane, cyclohexane, benzene, toluene, xylene, heptane and decane. Examples of the ketone-based solvent include acetone, methyl ethyl ketone, diethyl ketone, cyclohexanone and isophorone. Examples of the ester-based solvent include ethyl acetate, methyl acetate, ethyl succinate, methyl carbonate, ethyl benzoate and diethylene glycol diacetate. Examples of the ether-based solvent include diethyl ether, dibutyl ether, tetrahydrofuran, dioxane, diethylene glycol dimethyl ether, triethylene glycol diethyl ether and diphenyl ether.

Examples of the halogen-based solvent include dichloromethane, chloroform, tetrachloromethane, dichloroethane, 1,1',2,2'-tetrachloroethane, chlorobenzene and dichlorobenzene. Examples of the amide-based solvent include formamide, N,N-dimethylformamide, N,N-dimethylacetamide and N-methyl-2-pyrrolidone. These solvents may be used alone or as a mixture.

In the present invention, the solvent is used in an amount of 1 to 1,000 parts by weight based on 100 parts by weight of the total of the polymer compound and the cyclic carbodiimide compound. When the amount of the solvent is smaller than 1 part by weight, there is no significance of using the solvent. Although the upper limit of the amount of the solvent is not particularly limited, it is about 1,000 parts by weight from the viewpoints of manipulation ease and reaction efficiency.

In the case of the method in which the solid polymer compound is brought into contact with a liquid containing the cyclic carbodiimide compound dissolved therein, dispersed therein or molten therein to be impregnated with the cyclic carbodiimide compound, the solid polymer compound is brought into contact with the carbodiimide compound dissolved in the solvent, or the solid polymer compound is brought into contact with an emulsion of the cyclic carbodiimide compound. To bring the solid polymer compound into contact with the cyclic carbodiimide compound, the polymer compound is immersed in the cyclic carbodiimide compound, or coated or sprayed with the cyclic carbodiimide compound.

A sealing reaction by the cyclic carbodiimide compound of the present invention can be carried out at room temperature (25° C.) to 300° C. However, it is preferably 50 to 280° C., more preferably 100 to 280° C. from the viewpoint of reaction efficiency. Although the reaction proceeds more at a temperature at which the polymer compound is molten, the reaction is preferably carried out at a temperature lower than 300° C. to suppress the sublimation and decomposition of the cyclic carbodiimide compound. To reduce the melting temperature and increase the agitation efficiency of the polymer, use of the solvent is effective.

Although the reaction proceeds fully swiftly without a catalyst, a catalyst for promoting the reaction may be used. As the catalyst may be used a catalyst which is used for a conventional linear carbodiimide compound (JP-A 2005-2174). Examples of the catalyst include alkali metal compounds, alkali earth metal compounds, tertiary amine compounds, imidazole compounds, quaternary ammonium salts, phosphine compounds, phosphonium salts, phosphoric acid esters, organic acids and Lewis acid. They may be used alone or in combination of two or more. The amount of the catalyst which is not particularly limited is preferably 0.001 to 1 part by weight, more preferably 0.01 to 0.1 part by weight, much more preferably 0.02 to 0.1 part by weight based on 100 parts by weight of the total of the polymer compound and the cyclic carbodiimide compound.

As for the amount of the cyclic carbodiimide compound, the content of the carbodiimide group contained in the cyclic carbodiimide compound is selected from a range from 0.5 to 100 equivalents based on 1 equivalent of the acid group. When the content of the carbodiimide group is lower than 0.5 equivalent, there may be no significance of using the carbodiimide. When the content is higher than 100 equivalents, the characteristic properties of a matrix may change. From this viewpoint of view, the content of the carbodiimide group is preferably 0.6 to 75 equivalents, more preferably 0.65 to 50 equivalents, much more preferably 0.7 to 30 equivalents, particularly preferably 0.7 to 20 equivalents based on the above standard.

EXAMPLES

The following examples are provided to further illustrate the present invention. Physical properties were measured by the following methods.

(1) Identification of Cyclic Carbodiimide Structure by NMR

The synthesized cyclic carbodiimide compound was confirmed by $^1$H-NMR and $^{13}$C-NMR. The JNR-EX270 of JEOL Ltd. was used for NMR. Heavy chloroform was used as the solvent.

(2) Identification of Carbodiimide Skeleton of Cyclic Carbodiimide by IR

The existence of the carbodiimide skeleton of the synthesized cyclic carbodiimide compound at 2,100 to 2,200 cm$^{-1}$ which is the characteristic of a carbodiimide was confirmed by FT-IR. The Magna-750 of Thermonicoley Co., Ltd. was used for FT-IR.

(3) Concentration of Carboxyl Group

The sample was dissolved in purified o-cresol in a nitrogen stream and titrated with an ethanol solution of 0.05 N potassium hydroxide by using bromocresol blue as an indicator.

Example 1

Synthesis of Cyclic Carbodiimide CC1 (Scheme 1)

CC1: MW=252

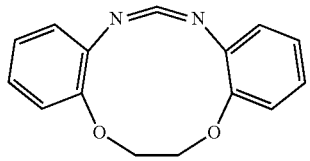 [SMILES: C1=Nc2ccccc2OCCOc2ccccc2N=1]

Step (1a)

o-nitrophenol (0.11 mol), 1,2-dibromoethane (0.05 mol), potassium carbonate (0.33 mol) and 200 ml of N,N-dimethylformamide were fed to a reactor equipped with a stirrer and a heater in an N$_2$ atmosphere and reacted at 130° C. for 12 hours, DMF was removed under reduced pressure, the obtained solid was dissolved in 200 ml of dichloromethane, and the resulting solution was separated with 100 ml of water 3 times. An organic layer was dehydrated with 5 g of sodium sulfate and dichloromethane was removed under reduced pressure to obtain an intermediate product A (nitro compound).

Step (2a)

Then, the intermediate product A (0.1 mol), 5% palladium carbon (Pd/C) (1 g) and 200 ml of ethanol/dichloromethane (70/30) were fed to a reactor equipped with a stirrer, hydrogen substitution was carried out 5 times, and a reaction was carried out while hydrogen was always supplied at 25° C. and terminated when the amount of hydrogen did not decrease any more. When Pd/C was collected and the mixed solvent was removed, an intermediate product B (amine compound) was obtained.

Step (3a)

Then, triphenylphosphine dibromide (0.11 mol) and 150 ml of 1,2-dichloroethane were fed to a reactor equipped with a stirrer, a heater and a dropping funnel in an N$_2$ atmosphere and stirred. A solution obtained by dissolving the intermediate product B (0.05 mol) and triethylamine (0.25 mol) in 50 ml of 1,2-dichloroethane was gradually added dropwise to the resulting mixture at 25° C. After the end of addition, a reaction was carried out at 70° C. for 5 hours. Thereafter, the reaction solution was filtered and the filtrate was separated with 100 ml of water 5 times. An organic layer was dehydrated with 5 g of sodium sulfate and 1,2-dichloroethane was removed under reduced pressure to obtain an intermediate product C (triphenylphosphine compound).

Step (4a)

Thereafter, di-tert-butyl dicarbonate (0.11 mol), N,N-dimethyl-4-aminopyridine (0.055 mol) and 150 ml of dichloromethane were fed to a reactor equipped with a stirrer and a dropping funnel in an N$_2$ atmosphere and stirred. 100 ml of dichloromethane containing the intermediate product C (0.05 mol) dissolved therein was gradually added dropwise to the resulting mixture at 25° C. After the end of addition, a reaction was carried out for 12 hours. Thereafter, a solid obtained by removing dichloromethane was purified to obtain CC1. The structure of CC1 was checked by NMR and IR.

Example 2

Synthesis of Cyclic Carbodiimide CC2 (Scheme 1)

CC2: MW=516

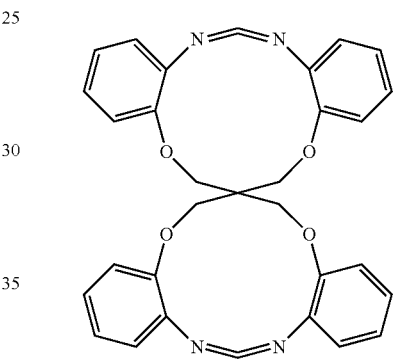

Step (1A)

o-nitrophenol (0.11 mol), pentaerythritol tetrabromide (0.025 mol), potassium carbonate (0.33 mol) and 200 ml of N,N-dimethylformamide were fed to a reactor equipped with a stirrer and a heater in an N$_2$ atmosphere and reacted at 130° C. for 12 hours, DMF was removed under reduced pressure, the obtained solid was dissolved in 200 ml of dichloromethane, and the resulting solution was separated with 100 ml of water 3 times. An organic layer was dehydrated with 5 g of sodium sulfate and dichloromethane was removed under reduced pressure to obtain an intermediate product D (nitro compound).

Step (2A)

Then, the intermediate product D (0.1 mol), 5% palladium carbon (Pd/C) (2 g) and 400 ml of ethanol/dichloromethane (70/30) were fed to a reactor equipped with a stirrer, hydrogen substitution was carried out 5 times, and a reaction was carried out while hydrogen was always supplied at 25° C. and terminated when the amount of hydrogen did not decrease any more. When Pd/C was collected and the mixed solvent was removed, an intermediate product E (amine compound) was obtained.

Step (3A)

Then, triphenylphosphine dibromide (0.11 mol) and 150 ml of 1,2-dichloroethane were fed to a reactor equipped with a stirrer, a heater and a dropping funnel in an N$_2$ atmosphere and stirred. A solution obtained by dissolving the intermediate product E (0.025 mol) and triethylamine (0.25 mol) in 50 ml of 1,2-dichloroethane was gradually added dropwise to the resulting mixture at 25° C. After the end of addition, a reaction was carried out at 70° C. for 5 hours. Thereafter, the reaction solution was filtered and the filtrate was separated with 100 ml of water 5 times. An organic layer was dehydrated with 5 g of sodium sulfate and 1,2-dichloroethane was removed under reduced pressure to obtain an intermediate product F (triphenylphosphine compound).

Step (4A)

Thereafter, di-tert-butyl dicarbonate (0.11 mol), N,N-dimethyl-aminopyridine (0.055 mol) and 150 ml of dichloromethane were fed to a reactor equipped with a stirrer and a dropping funnel in an $N_2$ atmosphere and stirred. 100 ml of dichloromethane containing the intermediate product F (0.025 mol) dissolved therein was gradually added dropwise to the resulting mixture at 25° C. After the end of addition, a reaction was carried out for 12 hours. Thereafter, a solid obtained by removing dichloromethane was purified to obtain CC2. The structure of CC2 was checked by NMR and IR.

Example 3

Synthesis of Cyclic Carbodiimide CC2 (Scheme 2)

Step (1A)

o-nitrophenol (0.11 mol), pentaerythritol tetrabromide (0.025 mol), potassium carbonate (0.33 mol) and 200 ml of N,N-dimethylformamide were fed to a reactor equipped with a stirrer and a heater in an $N_2$ atmosphere and reacted at 130° C. for 12 hours, N,N-dimethylformamide was removed under reduced pressure, the obtained solid was dissolved in 200 ml of dichloromethane, and the resulting solution was separated with 100 ml of water 3 times. An organic layer was dehydrated with 5 g of sodium sulfate and dichloromethane was removed under reduced pressure to obtain an intermediate product D (nitro compound).

Step (2A)

Then, the intermediate product D (0.1 mol), 5% palladium carbon (Pd/C) (1.25 g) and 500 ml of N,N-dimethylformamide were fed to a reactor equipped with a stirrer, hydrogen substitution was carried out 5 times, and a reaction was carried out while hydrogen was always supplied at 25° C. and terminated when the amount of hydrogen did not decrease any more. When Pd/C was collected by filtration and the filtrate was added to 3 liters of water, a solid separated out. This solid was collected and dried to obtain an intermediate product E (amine compound).

Step (3B)

Then, the intermediate product E (0.025 mol), imidazole (0.2 mol), carbon disulfide (0.2 mol) and 150 ml of 2-butanone were fed to a reactor equipped with a stirrer, a heater and a walter containing alkaline water in an $N_2$ atmosphere. This reaction solution was heated at 80° C. and reacted for 15 hours. After the reaction, the precipitated solid was collected by filtration and washed to obtain an intermediate product G (thiourea compound).

Step (4B)

Thereafter, the intermediate product G (0.025 mol), para-toluenesulfonyl chloride (0.1 mol) and 50 ml of pyridine were fed to a reactor equipped with a stirrer in an $N_2$ atmosphere and stirred. After a reaction was carried out at 25° C. for 3 hours, 150 ml of methanol was added and stirred at 25° C. for 1 hour. The precipitated solid was collected by filtration and washed to obtain CC2. The structure of CC2 was checked by NMR and IR.

Example 4

Synthesis of Cyclic Carbodiimide CC2 (Scheme 2)

Step (1A)

o-nitrophenol (0.11 mol), pentaerythritol tetrabromide (0.025 mol), potassium carbonate (0.33 mol) and 200 ml of N,N-dimethylformamide were fed to a reactor equipped with a stirrer and a heater in an $N_2$ atmosphere and reacted at 130° C. for 12 hours, N,N-dimethylformamide was removed under reduced pressure, the obtained solid was dissolved in 200 ml of dichloromethane, and the resulting solution was separated with 100 ml of water 3 times. An organic layer was dehydrated with 5 g of sodium sulfate and dichloromethane was removed in vacuum to obtain an intermediate product D (nitro compound).

Step (2A)

Then, the intermediate product D (0.1 mol), 5% palladium carbon (Pd/C) (1.25 g) and 500 ml of N,N-dimethylformamide were fed to a reactor equipped with a stirrer, hydrogen substitution was carried out 5 times, and a reaction was carried out while hydrogen was always supplied at 25° C. and terminated when the amount of hydrogen did not decrease any more. When Pd/C was collected by filtration and the filtrate was added to 3 liters of water, a solid separated out. This solid was collected and dried to obtain an intermediate product E (amine compound).

Step (3B)

Then, the intermediate product E (0.025 mol), imidazole (0.2 mol) and 125 ml of acetonitrile were fed to a reactor equipped with a stirrer, a heater and a dropping funnel in an $N_2$ atmosphere, and diphenyl phosphite (0.1 mol) was fed to the dropping funnel. After carbon dioxide substitution was carried out 5 times, diphenyl phosphite was gradually added dropwise while carbon dioxide was always supplied at 25° C. under agitation to carryout a reaction for 15 hours. After the reaction, the precipitated solid was collected by filtration and washed to obtain an intermediate product H (urea compound).

Step (4B)

Thereafter, the intermediate product H (0.025 mol), para-toluenesulfonyl chloride (0.1 mol) and 50 ml of pyridine were fed to a reactor equipped with a stirrer in an $N_2$ atmosphere and stirred. After a reaction was carried out at 25° C. for 3 hours, 150 ml of methanol was added and stirred at 25° C. for 1 hour. The precipitated solid was collected by filtration and washed to obtain CC2. The structure of CC2 was checked by NMR and IR.

Example 5

Synthesis of Cyclic Carbodiimide CC2 (Scheme 3)

Step (1B)

o-chloronitrobenzene (0.125 mol), pentaerythritol (0.025 mol), potassium carbonate (0.25 mol), tetrabutylammonium bromide (0.018 mol) and 50 ml of N,N-dimethylformamide were fed to a reactor equipped with a stirrer and a heater in an $N_2$ atmosphere and reacted at 130° C. for 12 hours. After the reaction, the resulting solution was added to 200 ml of water and the precipitated solid was collected by filtration. This solid was washed and dried to obtain an intermediate product D (nitro compound).

Step (2A)

Then, the intermediate product D (0.1 mol), 5% palladium carbon (Pd/C) (1.25 g) and 500 ml of N,N-dimethylformamide were fed to a reactor equipped with a stirrer, hydrogen substitution was carried out 5 times, and a reaction was carried out while hydrogen was always supplied at 25° C. and terminated when the amount of hydrogen did not decrease any more. When Pd/C was collected by filtration and the filtrate was added to 3 liters of water, a solid separated out. This solid was collected and dried to obtain an intermediate product E (amine compound).

Step (3B)

Then, the intermediate product E (0.025 mol), imidazole (0.2 mol) and 125 ml of acetonitrile were fed to a reactor equipped with a stirrer, a heater and a dropping funnel in an $N_2$ atmosphere, and diphenyl phosphite (0.1 mol) was fed to the dropping funnel. After carbon dioxide substitution was carried out 5 times, diphenyl phosphite was gradually added dropwise while carbon dioxide was always supplied at 25° C. under agitation to carry out a reaction for 15 hours. After the reaction, the precipitated solid was collected by filtration and washed to obtain an intermediate product H (urea compound).

Step (4B)

Thereafter, the intermediate product H (0.025 mol), para-toluenesulfonyl chloride (0.1 mol) and 50 ml of pyridine were fed to a reactor equipped with a stirrer in an $N_2$ atmosphere and stirred. After a reaction was carried out at 25° C. for 3 hours, 150 ml of methanol was added and stirred at 25° C. for 1 hour. The precipitated solid was collected by filtration and washed to obtain CC2. The structure of CC2 was checked by NMR and IR.

Example 6

Synthesis of Cyclic Carbodiimide CC2 (Scheme 3)

Step (1B)

o-chloronitrobenzene (0.125 mol), pentaerythritol (0.025 mol), potassium carbonate (0.25 mol), tetrabutylammonium bromide (0.018 mol) and 50 ml of N,N-dimethylformamide were fed to a reactor equipped with a stirrer and a heater in an $N_2$ atmosphere and reacted at 130° C. for 12 hours. After the reaction, the resulting solution was added to 200 ml of water and the precipitated solid was collected by filtration. This solid was cleaned and dried to obtain an intermediate product D (nitro compound).

Step (2A)

Then, the intermediate product D (0.1 mol), 5 palladium carbon (Pd/C) (1.25 g) and 500 ml of N,N-dimethylformamide were fed to a reactor equipped with a stirrer, hydrogen substitution was carried out 5 times, and a reaction was carried out while hydrogen was always supplied at 25° C. and terminated when the amount of hydrogen did not decrease any more. When Pd/C was collected by filtration and the filtrate was added to 3 liters of water, a solid separated out. This solid was collected and dried to obtain an intermediate product E (amine compound).

Step (3B)

Then, the intermediate product E (0.025 mol), imidazole (0.2 mol), carbon disulfide (0.2 mol) and 150 ml of 2-butanone were fed to a reactor equipped with a stirrer, a heater and a walter containing alkaline water in an $N_2$ atmosphere. This reaction solution was heated at 80° C. to be reacted for 15 hours. After the reaction, the precipitated solid was collected by filtration and washed to obtain an intermediate product G (thiourea compound).

Step (4B)

Thereafter, the intermediate product G (0.025 mol), para-toluenesulfonyl chloride (0.1 mol) and 50 ml of pyridine were fed to a reactor equipped with a stirrer in an $N_2$ atmosphere and stirred. After a reaction was carried out at 25° C. for 3 hours, 150 ml of methanol was added and stirred at 25° C. for 1 hour. The precipitated solid was collected by filtration and washed to obtain CC2. The structure of CC2 was checked by NMR and IR.

Example 7

Synthesis of Cyclic Carbodiimide CC2 (Scheme 4)

Step (1B)

o-chloronitrobenzene (0.125 mol), pentaerythritol (0.025 mol), potassium carbonate (0.25 mol), tetrabutylammonium bromide (0.018 mol) and 50 ml of N,N-dimethylformamide were fed to a reactor equipped with a stirrer and a heater in an $N_2$ atmosphere and reacted at 130° C. for 12 hours. After the reaction, the resulting solution was added to 200 ml of water and the precipitated solid was collected by filtration. This solid was washed and dried to obtain an intermediate product D (nitro compound).

Step (2A)

Then, the intermediate product D (0.1 mol), 5% palladium carbon (Pd/C) (1.25 g) and 500 ml of N,N-dimethylformamide were fed to a reactor equipped with a stirrer, hydrogen substitution was carried out 5 times, and a reaction was carried out while hydrogen was always supplied at 25° C. and terminated when the amount of hydrogen did not decrease any more. When Pd/C was collected by filtration and the filtrate was added to 3 liters of water, a solid separated out. This solid was collected and dried to obtain an intermediate product E (amine compound).

Step (3A)

Then, triphenylphosphine dibromide (0.11 mol) and 150 ml of 1,2-dichloroethane were fed to a reactor equipped with a stirrer, a heater and a dropping funnel in an $N_2$ atmosphere and stirred. A solution prepared by dissolving the intermediate product E (0.025 mol) and triethylamine (0.25 mol) in 50 ml of 1,2-dichloroethane was gradually added dropwise to this resulting mixture at 25° C. After the end of addition, a reaction was carried out at 70° C. for 5 hours. Thereafter, the reaction solution was filtered, and the filtrate was separated with 100 ml of water 5 times. An organic layer was dehydrated with 5 g of sodium sulfate and 1,2-dichloroethane was removed under reduced pressure to obtain an intermediate product F (triphenylphosphine compound).

Step (4A)

Thereafter, di-tert-butyl dicarbonate (0.11 mol), N,N-dimethyl-4-aminopyridine (0.055 mol) and 150 ml of dichloromethane were fed to a reactor equipped with a stirrer and a dropping funnel in an $N_2$ atmosphere and stirred. 100 ml of dichloromethane containing the intermediate product F (0.025 mol) dissolved therein was gradually added dropwise to the resulting mixture. After the addition, a reaction was carried out for 12 hours. A solid obtained by removing dichloromethane was purified to obtain CC2. The structure of CC2 was checked by NMR and IR.

Example 8

End-Sealing of Polylactic Acid by CC1

0.005 part by weight of tin octylate was added to 100 parts by weight of L-lactide (manufactured by Musashino Kagaku Kenkyuusho Co., Ltd., optical purity of 100%) to carry out a reaction at 180° C. in a reactor quipped with a stirring blade in a nitrogen atmosphere for 2 hours, phosphoric acid was added as a catalyst deactivator in an amount of 1.2 times the equivalent of tin octylate, the residual lactide was removed at 13.3 Pa, and the residue was formed into a chip to obtain poly(L-lactic acid). The carboxyl group concentration of the obtained poly(L-lactic acid) was 14 eq/ton.

100 parts by weight of the obtained poly(L-lactic acid) and 0.5 part by weight of CC1 were melt kneaded together by means of a double-screw extruder (cylinder temperature of 230° C.) for a residence time of 3 minutes. The carboxyl group concentration was reduced to not more than 0.4 eq/ton. There was no smell of an isocyanate at the outlet of the extruder after kneading.

Example 9

End-Sealing of Polylactic Acid by CC2

When a reaction was carried out in the same manner as in Example 8 except that the cyclic carbodiimide CC1 was changed to the cyclic carbodiimide CC2, the carboxyl group concentration was reduced to not more than 0.3 eq/ton. There was no smell of an isocyanate at the outlet of the extruder after kneading.

Comparative Example 1

End-Sealing of Polylactic Acid by Linear Carbodiimide Compound

When a reaction was carried out in the same manner as in Example 8 except that the cyclic carbodiimide CC1 was changed to the "Stabacsole I" linear carbodiimide of Line Chemie Japan Co., Ltd., the carboxyl group concentration was 0.4 eq/ton but a strong bad smell of an isocyanate was produced at the outlet of the extruder.

Example 10

End-Sealing of Polyamide by CC2

Polymetaxylene adipamide (MX Nylon S6001 of Mitsubishi Gas Chemical Co., Ltd.) is a polyamide comprising metaxylylenediamine and adipic acid and had a carboxyl group concentration of 70 eq/ton. 100 parts by weight of this polymetaxylylene adipamide and 2.0 part by of CC2 were melt kneaded together by means of a double-screw extruder (cylinder temperature of 260° C.) for a residence time of 3 minutes. The carboxyl group concentration was reduced to not more than 1.2 eq/ton. There was no smell of an isocyanate at the outlet of the extruder after kneading.

Comparative Example 2

End-Sealing of Polyamide by Linear Carbodiimide Compound

When a reaction was carried out in the same manner as in Example 8 except that the cyclic carbodiimide CC2 was changed to the "Stabacsole I" linear carbodiimide of Line Chemie Japan Co., Ltd., the carboxyl group concentration was 2.2 eq/ton but a strong bad smell of an isocyanate was produced at the outlet of the extruder.

EFFECT OF THE INVENTION

The cyclic carbodiimide compound of the present invention can stabilize the hydrolyzable component of a polymer compound effectively. At this point, the side-production of a free isocyanate compound can be suppressed. The cyclic carbodiimide compound of the present invention can suppress the production of a bad smell from the isocyanate compound even when it seals the terminal of the polymer compound, thereby not deteriorating the work environment. When the terminal of the polymer compound is sealed by the cyclic carbodiimide compound, an isocyanate group is formed at the terminal of the polymer compound, and the molecular weight of the polymer compound can be increased by a reaction of the isocyanate group.

The cyclic carbodiimide compound of the present invention also has the function of capturing a free monomer and a compound having an acid group contained in the polymer compound.

Further, since the cyclic carbodiimide compound of the present invention has a cyclic structure, it can seal a terminal under a more mild condition than that of a linear carbodiimide compound.

By the production process of the present invention, a cyclic carbodiimide can be easily produced. The cyclic carbodiimide compound of the present invention is useful as an end-sealing agent for polymer compounds. The cyclic carbodiimide compound of the present invention is useful as a capture agent for acid groups, especially a free compound contained in a polymer compound.

The difference between a linear carbodiimide compound and a cyclic carbodiimide compound in the end-sealing reaction mechanism is described below.

When the linear carbodiimide compound ($R_1$—N=C=N—$R_2$) is used as an end-sealing agent for a polymer compound having a carboxyl group terminal, a reaction represented by the following formula takes place. In the formula, W is the main chain of the polymer compound. An amide group is formed at a terminal of the polymer compound through a reaction between the linear carbodiimide compound and the carboxyl group, and an isocyanate compound ($R_1$NCO) is liberated.

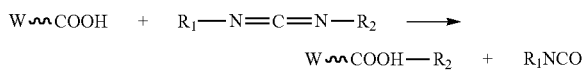

Meanwhile, when the cyclic carbodiimide compound is used as an end-sealing agent for a polymer compound having a carboxyl group terminal, a reaction represented by the following formula takes place. It is understood that an isocyanate group (—NCO) is formed at a terminal of the polymer compound via an amide group through a reaction between the cyclic carbodiimide compound and the carboxyl group and that an isocyanate compound is not liberated.

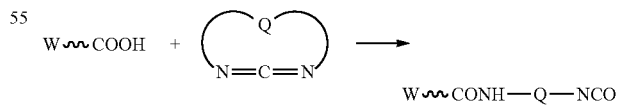

(in the above formula, Q is an aliphatic, alicyclic or aromatic group or a divalent to tetravalent bond group which is a combination thereof, which may contain a hetero atom or a substituent.)

When two or more carbodiimides are contained in one ring, an isocyanate compound is disadvantageously liberated by a reaction of the carbodiimide group.

INDUSTRIAL APPLICABILITY

The cyclic carbodiimide compound of the present invention is advantageously used to stabilize an organic polymer compound having a hydrolyzable functional group as a constituent component.

The invention claimed is:

1. A cyclic carbodiimide compound represented by the following formula (i):

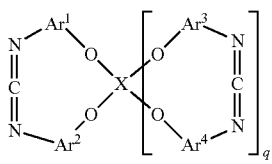
(i)

in the above formula, X is any one of divalent groups represented by the following formulas (i-1) to (i-3) or a tetravalent group represented by the following formula (i-4), when X is divalent, q is 0 and when X is tetravalent, q is 1, and $Ar^1$ to $Ar^4$ are each independently an aromatic group and may be substituted by an alkyl group having 1 to 6 carbon atoms or phenyl group

(i-1)

in the above formula, n is an integer of 1 to 6

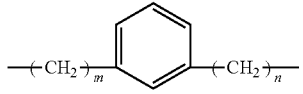
(i-2)

in the above formula, m and n are each independently an integer of 0 to 3

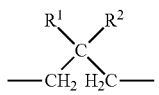
(i-3)

in the above formula, $R^1$ and $R^2$ are each independently an alkyl group having 1 to 6 carbon atoms or phenyl group

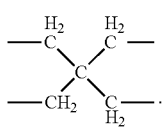
(i-4)

2. The compound according to claim 1, wherein $Ar^1$ to $Ar^4$ are each independently an orthophenylene group or 1,2-naphthalene-diyl group which may be substituted by an alkyl group having 1 to 6 carbon atoms or phenyl group.

3. A process of producing the cyclic carbodiimide compound of claim 1, comprising the steps of:

(1) (1a) reacting a compound of the following formula (a-1), a compound of the following formula (a-2) and a compound of the following formula (b-1) to obtain a nitro compound represented by the following formula (c):

(a-1)

(a-2)

(b-1)

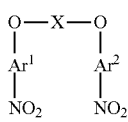
(c)

$E^1$ and $E^2$ are each independently a group selected from the group consisting of halogen atom, toluenesulfonyloxy group, methanesulfonyloxy group, benzenesulfonyloxy group and p-bromobenzenesulfonyloxy group);

(2) (2a) reducing the obtained nitro compound to obtain an amine compound represented by the following formula (d):

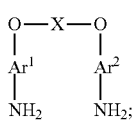
(d)

(3) (3a) reacting the obtained amine compound with triphenylphosphine dibromide to obtain a triphenylphosphine compound represented by the following formula (e-1):

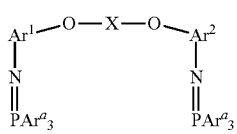
(e-1)

$Ar^a$ is a phenyl group; and (4) (4a) isocyanating the obtained triphenylphosphine compound in a reaction system and then decarbonating the isocyanated product directly to obtain a compound of the following formula (f):

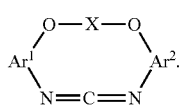
(f)

4. The process according to claim 3, wherein the step (1a) is the step (1b) of reacting a compound of the following formula (a-i), a compound of the following formula (a-ii) and a compound of the following formula (b-i):

(a-i)

(a-ii)

(b-i)

$E^3$ and $E^4$ are each independently a group selected from the group consisting of halogen atom, toluenesulfonyloxy group, methanesulfonyloxy group, benzenesulfonyloxy group and p-bromobenzenesulfonyloxy group).

5. The process according to claim 3, wherein the step (3a) is the step (3b) of reacting an amine compound with carbon dioxide or carbon disulfide to obtain an urea compound or thiourea compound represented by the following formula (e-2):

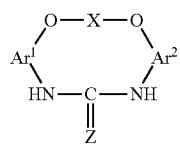

(e-2)

Z is an oxygen atom or sulfur atom); and the step (4a) is the step (4b) of dehydrating the obtained urea compound or desulfurizing the thiourea compound.

6. A process of producing the cyclic carbodiimide compound of claim 1, comprising the steps of:
(1) (1A) reacting compounds of the following formulas (A-1) to (A-4) and a compound of the following formula (B-1) to obtain a nitro compound of the following formula (C);

 (A-1)

 (A-2)

 (A-3)

 (A-4)

 (B-1)

$X_1$ is

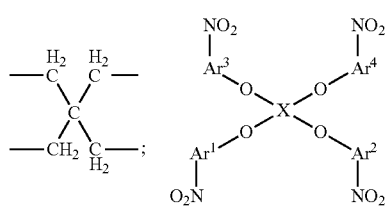 (C)

$E^1$ to $E^4$ are each independently a group selected from the group consisting of halogen atom, toluenesulfonyloxy group, methanesulfonyloxy group, benzenesulfonyloxy group and p-bromobenzenesulfonyloxy group);

(2) (2A) reducing the obtained nitro compound to obtain an amine compound of the following formula (D):

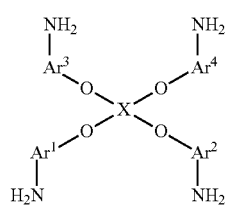 (D)

(3) (3A) reacting the obtained amine compound with triphenylphosphine dibromide to obtain a triphenylphosphine compound of the following formula (E-1):

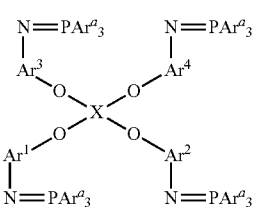 (E-1)

$Ar^a$ is a phenyl group; and (4) (4A) isocyanating the obtained triphenylphosphine compound in a reaction system and then decarbonating the isocyanated product directly to obtain a compound of the following formula (F):

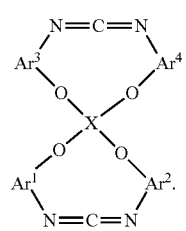 (F)

7. The process according to claim 6, wherein the step (1A) is the step (1B) of reacting compounds of the following formulas (A-i) to (A-iv) and a compound of the following formula (B-i) to obtain a nitro compound of the formula (C):

 (A-i)

 (A-ii)

 (A-iii)

 (A-iv)

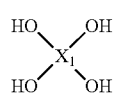 (B-i)

$X_1$ is

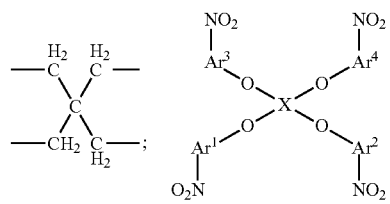 (C)

$E^5$ to $E^8$ are each independently a group selected from the group consisting of halogen atom, toluenesulfonyloxy group, methanesulfonyloxy group, benzenesulfonyloxy group and p-bromobenzenesulfonyloxy group).

8. The process according to claim 6, wherein the step (3A) is the step (3B) of reacting an amine compound with carbon dioxide or carbon disulfide to obtain an urea compound or thiourea compound of the following formula (E-2):

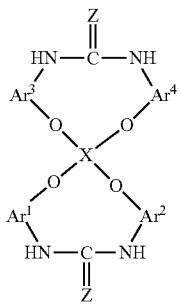
(E-2)

Z is an oxygen atom or sulfur atom); and the step (4A) is the step (4B) of dehydrating the obtained urea compound or desulfurizing the thiourea compound.

9. An end-sealing agent for polymer compounds, which comprises a cyclic carbodiimide compound as an active ingredient, wherein the cyclic carbodiimide compound is represented by the following formula (i):

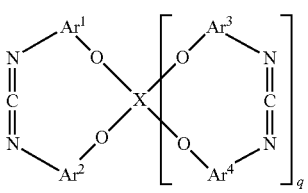
(i)

in the above formula, X is any one of divalent groups represented by the following formulas (i-1) to (i-3) or a tetravalent group represented by the following formula (i-4), when X is divalent, q is 0 and when X is tetravalent, q is 1, and $Ar^1$ to $Ar^4$ are each independently an aromatic group and may be substituted by an alkyl group having 1 to 6 carbon atoms or phenyl group

(i-1)

in the above formula, n is an integer of 1 to 6

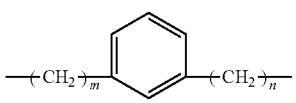
(i-2)

in the above formula, m and n are each independently an integer of 0 to 3

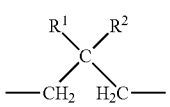
(i-3)

in the above formula, $R^1$ and $R^2$ are each independently an alkyl group having 1 to 6 carbon atoms or phenyl group

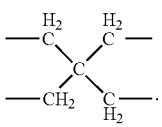
(i-4)

10. A capture agent for an acid group, which comprises a cyclic carbodiimide compound as an active ingredient, wherein the cyclic carbodiimide compound is represented by the following formula (i):

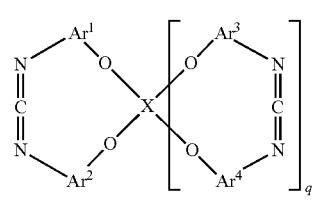
(i)

in the above formula, X is any one of divalent groups represented by the following formulas (i-1) to (i-3) or a tetravalent group represented by the following formula (i-4), when X is divalent, q is 0 and when X is tetravalent, q is 1, and $Ar^1$ to $Ar^4$ are each independently an aromatic group and may be substituted by an alkyl group having 1 to 6 carbon atoms or phenyl group

(i-1)

in the above formula, n is an integer of 1 to 6

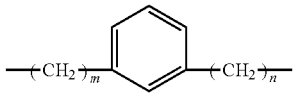
(i-2)

in the above formula, m and n are each independently an integer of 0 to 3

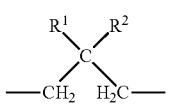
(i-3)

in the above formula, $R^1$ and $R^2$ are each independently an alkyl group having 1 to 6 carbon atoms or phenyl group

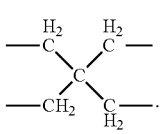
(i-4)

11. The process according to claim 4, wherein the step (3a) is the step (3b) of reacting an amine compound with carbon dioxide or carbon disulfide to obtain an urea compound or thiourea compound represented by the following formula (e-2):

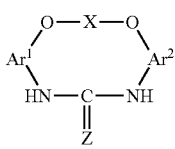
(e-2)

Z is an oxygen atom or sulfur atom); and the step (4a) is the step (4b) of dehydrating the obtained urea compound or desulfurizing the thiourea compound.

12. The process according to claim 7, wherein the step (3A) is the step (3B) of reacting an amine compound with carbon dioxide or carbon disulfide to obtain an urea compound or thiourea compound of the following formula (E-2):

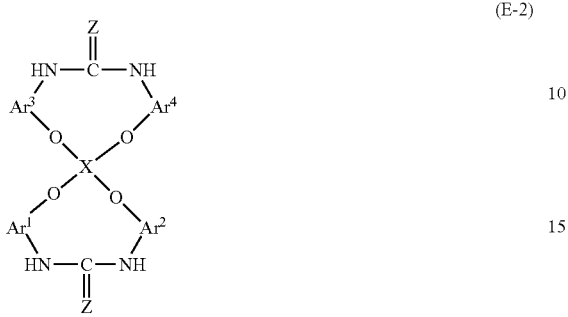

(E-2)

in the above formula, $Ar^1$ to $Ar^4$ and X are as defined in the above formula (i), and Z is an oxygen atom or sulfur atom; and the step (4A) is the step (4B) of dehydrating the obtained urea compound or desulfurizing the thiourea compound.

* * * * *